United States Patent
Tojo et al.

(10) Patent No.: US 9,222,101 B2
(45) Date of Patent: Dec. 29, 2015

(54) METHOD OF PRODUCING FATTY ACIDS OR LIPIDS CONTAINING FATTY ACIDS USING THIOESTERASE VARIANTS

(75) Inventors: Takuto Tojo, Haga-Gun (JP); Keiji Endo, Haga-gun (JP)

(73) Assignee: KAO CORPORATION, Tokyo (JP)

( * ) Notice: Subject to any disclaimer, the term of this patent is extended or adjusted under 35 U.S.C. 154(b) by 641 days.

(21) Appl. No.: 13/516,047

(22) PCT Filed: Dec. 3, 2010

(86) PCT No.: PCT/JP2010/071717
§ 371 (c)(1),
(2), (4) Date: Jun. 14, 2012

(87) PCT Pub. No.: WO2011/077931
PCT Pub. Date: Jun. 30, 2011

(65) Prior Publication Data
US 2013/0219557 A1 Aug. 22, 2013

(30) Foreign Application Priority Data

Dec. 25, 2009 (JP) .................................. 2009-295458
Oct. 7, 2010 (JP) .................................. 2010-227262

(51) Int. Cl.
C07K 14/00 (2006.01)
C12N 15/82 (2006.01)
C07K 14/415 (2006.01)
C12N 9/16 (2006.01)
C12P 7/64 (2006.01)

(52) U.S. Cl.
CPC .......... *C12N 15/8247* (2013.01); *C07K 14/415* (2013.01); *C12N 9/16* (2013.01); *C12N 15/8218* (2013.01); *C12N 15/8285* (2013.01); *C12P 7/6463* (2013.01)

(58) Field of Classification Search
None
See application file for complete search history.

(56) References Cited

U.S. PATENT DOCUMENTS

| | | | |
|---|---|---|---|
| 5,925,805 | A | 7/1999 | Ohlrogge et al. |
| 5,955,329 | A | 9/1999 | Yuan et al. |
| 2004/0093638 | A1 | 5/2004 | Sasaki et al. |

FOREIGN PATENT DOCUMENTS

| | | |
|---|---|---|
| JP | 11-506323 | 6/1999 |
| JP | 2002-335786 A | 11/2002 |
| WO | WO 91-16421 | 10/1991 |
| WO | WO 96/36719 | 11/1996 |
| WO | WO 96/38573 | 12/1996 |
| WO | WO 00/36114 A2 | 6/2000 |
| WO | WO 2008/076377 A2 | 6/2008 |

OTHER PUBLICATIONS

L Yuan, T A Voelker, and D J Hawkins. Modification of the substrate specificity of an acyl-acyl carrier protein thioesterase by protein engineering. Proc Natl Acad Sci U S A. 92(23): 10639-10643. Nov. 7, 1995.*
Voelker, Toni A.; Worrell, Ann C.; Anderson, Lana; Bleibaum, Janice; Fan, Calvin; Hawkins, Deborah J.; Radke, Sharon E.; Maelor Davies, H. Fatty Acid Biosynthesis Redirected to Medium Chains in Transgenic Oilseed Plants. Science, vol. 257, Issue 5066, pp. 72-74. Jul. 3, 1992.*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
International Search Report (ISR) for PCT/JP2010/071717, I.A. fd: Dec. 3, 2010, mailed Feb. 1, 2011 from the Japanese Patent Office, Tokyo, Japan.
International Preliminary Report on Patentability (IPRP), Chapter I of the Patent Cooperation Treaty, including the Written Opinion for PCT/JP2010/071717, I.A. fd: Dec. 3, 2010, issued Aug. 14, 2012, from the International Bureau of WIPO, Geneva, Switzerland.
Jako, C et al., "Seed-Specific Over-Expression of an Arabidopsis cDNA Encoding a Diacylglycerol Acyltransferase Enhances Seed Oil Content and Seed Weight," Plant Physiology, Jun. 2001; 126:861-874, Am Soc Plant Physiologists, Rockville, MD.
Madoka, Y, et al., "Chloroplast Transformation with Modified accD Operon Increases Acetyl-CoA Carboxylase and Causes Extension of Leaf Longevity and Increase in Seed Yield in Tobacco," Plant Cell Physiol., Dec. 2002; 43:1518-1525, Oxford Univ. Press, Tokyo, Japan.
Voelker, TA et al., "Alteration of the specificity and regulation of fatty acid synthesis of *Escherichia coli* by expression of a plant medium-chain acyl-acyl carrier protein thioesterase," J. Bacteriol., Dec. 1994; 176:7320-7327, Am Soc Microbiol, Washington, DC.
Voelker, TA et al., "Fatty acid biosynthesis redirected to medium chains in transgenic oilseed plants," Science, Jul. 1992; 257:72-74, Am Assoc Adv Science, Washington, DC.
Voelker, TA et al., "Genetic engineering of a quantitative trait: metabolic and genetic parameters influencing the accumulation of laurate in rapeseed," The Plant Journal, Feb. 1996, 9:229-241, Blackwell Scientific Publishers, Oxford, England.
Yuan, L et al., "Modification of the substrate specifically of an acyl-acyl carrier protein thioesterase by protein engineering," Proc Natl Acad Sci USA, Nov. 1995; 92:10639-10643, National Academy of Sciences, Washington, DC.
Zou, J et al., "Modification of Seed Oil Content and Acyl Composition in the Brassicaceae by Expression of a Yeast sn-2 Acyltransferase Gene," Plant Cell, Jun. 1997; 9:909-923, Am Soc Plant Physiologists, Rockvile, MD.
Roble, ND et al., "L-Lactic acid production from raw cassava starch in a circulating loop bioreactor with cells immobilized in loofa (Luffa cylindrica)," Biotechnol Lett, Jul. 2003; 25(13): 1093-1098, Kluwer Academic Publishers, Dordrecht, Netherlands.

* cited by examiner

*Primary Examiner* — Medina A Ibrahim
*Assistant Examiner* — Wayne Zhong
(74) *Attorney, Agent, or Firm* — Sterne, Kessler, Goldstein & Fox P.L.L.C.

(57) ABSTRACT

A method of producing a fatty acid or a lipid containing a fatty acid, using a thioesterase variant having an amino acid sequence in which the $231^{st}$ amino acid is substituted from threonine to lysine in the amino acid sequence set forth in SEQ ID NO: 1; and a transformant obtained by introducing a gene that encodes the thioesterase variant which transformant has an enhanced ability to produce a fatty acid or a lipid containing a fatty acid.

20 Claims, 2 Drawing Sheets

SEQUENCE LISTING

<160> NUMBER OF SEQ ID NOS: 30

<210> SEQ ID NO 1
<211> LENGTH: 382
<212> TYPE: PRT
<213> ORGANISM: Umbellularia californica

<400> SEQUENCE: 1

```
Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
 50                  55                  60

Met Leu Phe Ala Val Ile Thr Thr Ile Phe Ser Ala Ala Glu Lys Gln
 65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365
```

Ser Phe Arg Gly Ile Ser Val Ile Pro Ala Glu Pro Arg Val
       370                 375                 380

<210> SEQ ID NO 2
<211> LENGTH: 1149
<212> TYPE: DNA
<213> ORGANISM: Umbellularia californica

<400> SEQUENCE: 2

```
atggccacca cctctttagc ttccgctttc tgctcgatga aagctgtaat gttggctcgt     60
gatggccggg gcatgaaacc caggagcagt gatttgcagc tgagggcggg aaatgcgcca    120
acctctttga agatgatcaa tgggaccaag ttcagttaca cggagagctt gaaaaggttg    180
cctgactgga gcatgctctt tgcagtgatc acaaccatct tttcggctgc tgagaagcag    240
tggaccaatc tagagtggaa gccgaagccg aagctacccc agttgcttga tgaccatttt    300
ggactgcatg ggttagtttt caggcgcacc tttgccatca gatcttatga ggtgggacct    360
gaccgctcca catctatact ggctgttatg aatcacatgc aggaggctac acttaatcat    420
gcgaagagtg tgggaattct aggagatgga ttcgggacga cgctagagat gagtaagaga    480
gatctgatgt gggttgtgag acgcacgcat gttgctgtgg aacggtaccc tacttggggt    540
gatactgtag aagtagagtg ctggattggt gcatctggaa ataatggcat gcgacgtgat    600
ttccttgtcc gggactgcaa acaggcgaaa attcttacaa gatgtaccag cctttcggtg    660
ctgatgaata aggacaag gaggttgtcc acaatccctg acgaagttag aggggagata    720
gggcctgcat tcattgataa tgtggctgtc aaggacgatg aaattaagaa actacagaag    780
ctcaatgaca gcactgcaga ttacatccaa ggaggtttga ctcctcgatg gaatgatttg    840
gatgtcaatc agcatgtgaa caacctcaaa tacgttgcct gggtttttga accgtcccca    900
gactccatct ttgagagtca tcatatttcc agcttcactc ttgaatacag gagagagtgc    960
acgagggata gcgtgctgcg gtccctgacc actgtctctg gtggctcgtc ggaggctggg   1020
ttagtgtgcg atcacttgct ccagcttgaa ggtgggtctg aggtattgag ggcaagaaca   1080
gagtggaggc ctaagcttac cgatagtttc agagggatta gtgtgatacc cgcagaaccg   1140
agggtgtaa                                                          1149
```

<210> SEQ ID NO 3
<211> LENGTH: 382
<212> TYPE: PRT
<213> ORGANISM: Umbellularia californica

<400> SEQUENCE: 3

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

```
Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Lys Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380

<210> SEQ ID NO 4
<211> LENGTH: 1149
<212> TYPE: DNA
<213> ORGANISM: Umbellularia californica

<400> SEQUENCE: 4
atggccacca cctctttagc ttccgctttc tgctcgatga aagctgtaat gttggctcgt      60
gatggccggg gcatgaaacc caggagcagt gatttgcagc tgagggcggg aaatgcgcca     120
acctctttga agatgatcaa tgggaccaag ttcagttaca cggagagctt gaaaaggttg     180
cctgactgga gcatgctctt tgcagtgatc acaaccatct tttcggctgc tgagaagcag     240
tggaccaatc tagagtggaa gccgaagccg aagctacccc agttgcttga tgaccatttt     300
ggactgcatg gttagtttt caggcgcacc tttgccatca gatcttatga ggtgggacct     360
gaccgctcca catctatact ggctgttatg aatcacatgc aggaggctac acttaatcat     420
gcgaagagtg tgggaattct aggagatgga ttcgggacga cgctagagat gagtaagaga     480
gatctgatgt gggttgtgag acgcacgcat gttgctgtgg aacggtaccc tacttggggt     540
gatactgtag aagtagagtg ctggattggt gcatctggaa ataatggcat gcgacgtgat     600
```

-continued

```
ttccttgtcc gggactgcaa aacaggcgaa attcttacaa gatgtaccag cctttcggtg    660
ctgatgaata caaggacaag gaggttgtcc aagatccctg acgaagttag agggagata     720 gggcctgcat tcattgataa tgtggctgtc aaggacgatg aaattaagaa actacagaag    780
ctcaatgaca gcactgcaga ttacatccaa ggaggtttga ctcctcgatg gaatgatttg    840
gatgtcaatc agcatgtgaa caacctcaaa tacgttgcct gggttttttga accgtccca    900 gactccatct tgagagtca tcatatttcc agcttcactc ttgaatacag agagagtgc      960 acgagggata gcgtgctgcg gtccctgacc actgtctctg gtggctcgtc ggaggctggg   1020
ttagtgtgcg atcacttgct ccagcttgaa ggtgggtctg aggtattgag ggcaagaaca   1080
gagtggaggc ctaagcttac cgatagtttc agagggatta gtgtgatacc cgcagaaccg   1140
agggtgtaa                                                           1149
```

<210> SEQ ID NO 5
<211> LENGTH: 43
<212> TYPE: DNA
<213> ORGANISM: Artificial
<220> FEATURE:
<223> OTHER INFORMATION: oligonucleotide primer No 1 for E coli

<400> SEQUENCE: 5

```
ggaaaaggtg gtgaactact atgtctagag tggaagccga agc                      43
```

<210> SEQ ID NO 6
<211> LENGTH: 27
<212> TYPE: DNA
<213> ORGANISM: Artificial
<220> FEATURE:
<223> OTHER INFORMATION: oligonucleotide primer No 2 for E coli

<400> SEQUENCE: 6

```
ttaatctaga ctgcagcttc taaaaag                                        27
```

<210> SEQ ID NO 7
<211> LENGTH: 31
<212> TYPE: DNA
<213> ORGANISM: Artificial
<220> FEATURE:
<223> OTHER INFORMATION: oligonucleotide primer No 3 for E coli

<400> SEQUENCE: 7

```
aagatccctg acgaagttag agggagata g                                    31
```

<210> SEQ ID NO 8
<211> LENGTH: 41
<212> TYPE: DNA
<213> ORGANISM: Artificial
<220> FEATURE:
<223> OTHER INFORMATION: oligonucleotide primer No 4 for E coli

<400> SEQUENCE: 8

```
ctctaacttc gtcagggatc ttggacaacc tccttgtcct t                        41
```

<210> SEQ ID NO 9
<211> LENGTH: 1747
<212> TYPE: DNA
<213> ORGANISM: Brassica rapa

<400> SEQUENCE: 9

```
gatatcacta caatgtcgga gagacaaggc tgcgccagca tatacaaaag ggaaatgaag    60
```

-continued

```
atggcctttt gattagctgt gtagcatcag cagctaatct ctgggctctc atcatggatg      120
ctggaactgg attcacttct caagtttatg agttgtcacc ggtcttccta cacaaggtaa      180
taatcagttg aagcaattaa gaatcaattt gatttgtagt aaactaagaa gaacttacct      240
tatgttttcc ccgcaggact ggattatgga acaatgggaa aagaactact atataagctc      300
catagctggt tcagataacg ggagctcttt agttgttatg tcaaaaggtt agtgtttagt      360
gaataataaa cttataccac aaagtcttca ttgacttatt tatatacttg ttgtgaattg      420
ctaggaacta cttattctca gcagtcatac aaagtgagtg actcatttcc gttcaagtgg      480
ataaataaga aatggaaaga agattttcat gtaacctcca tgacaactgc tggtaatcgt      540
tggggtgtgg taatgtcgag gaactctggc ttctctgatc aggtaggttt ttgtctctta      600
tggtctgggg gttttttattt ccctgatag tctaatatga taaactctgc gttgtgaaag      660
gtggtggagc ttgactttt gtacccaagc gatgggatac ataggaggtg ggagaatggg      720
tatagaataa catcaatggc agcaactgcg gatcaagcag ctttcatatt aagcataccaa     780 aagcgtaaga tggtggatga aactcaagag actctccgca ccaccgcctt tccaagtact      840
catgtcaagg ttggttttctt tagctttgaa cacagatttg gatctttttg ttttgtttcc     900
atatacttag gacctgagag cttttggttg attttttttt caggacaaat gggcgaagaa      960
tctgtacatt gcatcaatat gctatggcag gacagtgtgc tgatacacac ttaagcatca    1020
tgtggaaagc caaagacaat tggagcgaga ctcagggtcg tcataatacc aatcaaagac    1080
gtaaaaccag acgcaacctc tttggttgaa tgtaatgaaa gggatgtgtc ttggtatgta    1140
tgtacgaata acaaaagaga agatggaatt agtagtagaa atatttggga gcttttttaag   1200 cccttcaagt gtgcttttta tcttattgat atcatccatt tgcgttgttt aatgcgtctc    1260
tagatatgtt cctatatctt tctcagtgtc tgataagtga aatgtgagaa accatacca     1320 aaccaaaata ttcaaatctt attttttaata atgttgaatc actcggagtt gccaccttct   1380
gtgccaattg tgctgaatct atcacactag aaaaaaacat ttcttcaagg taatgacttg    1440
tggactatgt tctgaattct cattaagttt ttattttctg aagtttaagt ttttaccttc    1500
tgttttgaaa tatatcgttc ataagatgtc acgccaggac atgagctaca catcgcacat    1560
agcatgcaga tcaggacgat ttgtcactca cttcaaacac ctaagagctt ctctctcaca    1620
gcgcacacac atatgcatgc aatatttaca cgtgatcgcc atgcaaatct ccattctcac    1680
ctataaatta gagcctcggc ttcactcttt actcaaacca aaactcatca ctacagaaca    1740
tacacaa                                                              1747
```

<210> SEQ ID NO 10
<211> LENGTH: 1255
<212> TYPE: DNA
<213> ORGANISM: Brassica rapa

<400> SEQUENCE: 10

```
gtgtgtatac cacggtgata tgagtgtggt tgttgatgta tgttaacact acatagtcat       60
ggtgtgtgtt ccataaataa tgtactaatg taataagaac tactccgtag acggtaataa      120
aagagaagtt tttttttta ctcttgctac tttcctataa agtgatgatt aacaacagat       180
acaccaaaaa gaaaacaatt aatctatatt cacaatgaag cagtactagt ctattgaaca      240
tgtcagattt tctttttcta aatgtctaat taagccttca aggctagtga tgataaaaga      300
tcatccaatg ggatccaaca aagactcaaa tctggttttg atcagatact tcaaaactat      360
ttttgtattc attaaattat gcaagtgttc ttttatttgg tgaagactct ttagaagcaa      420
```

```
agaacgacaa gcagtaataa aaaaaacaaa gttcagtttt aagatttgtt attgacttat      480
tgtcatttga aaatatagt atgatattaa tatagttta tttatataat gcttgtctat      540
tcaagatttg agaacattaa tatgatactg tccacatatc caatatatta agtttcattt      600
ctgttcaaac atatgataga tggtcaaatg attatgagtt ttgttattta cctgaagaaa      660
gataagtgag cttcgagttt ctgaagggta cgtgatcttc atttcttggc taaaagcgaa      720
tatgacatca cctagagaaa gccgataata gtaaactctg ttcttggttt ttggtttaat      780
caaaccgaac cggtagctga gtgtcaagtc agcaaacatc gcaaaccata tgtcaattcg      840
ttagattccc ggtttaagtt gtaaaccggt atttcatttg gtgaaaaccc tagaagccag      900 ccacccttt taatctaatt tttgtaaacg agaagtcacc acacctctcc actaaaaccc      960
tgaaccttac tgagagaagc agagcgcagc tcaaagaaca aataaaaccc gaagatgaga     1020
ccaccacgtg gcggcgggag cttcagggga cggggaggaa gagatggcgg cggacgcttt     1080
ggtggcggcg gcggacgttt tggtggcggc ggtggacgct tggtggcgg cggtggacgc     1140 tttggtggtg gtggatatcg tgacgaaggg cctcccagcg aagtcattgg ttcgtttact     1200
ctttacttag tcgaatctta ttcttgctct gctcgttgtt ttaccgataa agctt         1255

<210> SEQ ID NO 11
<211> LENGTH: 240
<212> TYPE: DNA
<213> ORGANISM: Umbellularia californica

<400> SEQUENCE: 11
atggccacca cctctttagc ttccgctttc tgctcgatga aagctgtaat gttggctcgt       60
gatggccggg gcatgaaacc caggagcagt gatttgcagc tgagggcggg aaatgcgcca      120
acctctttga agatgatcaa tgggaccaag ttcagttaca cggagagctt gaaaaggttg      180
cctgactgga gcatgctctt tgcagtgatc acaaccatct tttcggctgc tgagaagcag      240

<210> SEQ ID NO 12
<211> LENGTH: 30
<212> TYPE: DNA
<213> ORGANISM: Artificial
<220> FEATURE:
<223> OTHER INFORMATION: oligonucleotide primer No 1 for Arabidopsis
      thaliana

<400> SEQUENCE: 12
gatatcacta caatgtcgga gagacaaggc                                        30

<210> SEQ ID NO 13
<211> LENGTH: 30
<212> TYPE: DNA
<213> ORGANISM: Artificial
<220> FEATURE:
<223> OTHER INFORMATION: oligonucleotide primer No 2 for Arabidopsis
      thaliana

<400> SEQUENCE: 13
ttgtgtatgt tctgtagtga tgagttttgg                                        30

<210> SEQ ID NO 14
<211> LENGTH: 28
<212> TYPE: DNA
<213> ORGANISM: Artificial
<220> FEATURE:
<223> OTHER INFORMATION: oligonucleotide primer No 3 for Arabidopsis
      thaliana
```

-continued

<400> SEQUENCE: 14
agtgtgtata ccacggtgat atgagtgt                                           28

<210> SEQ ID NO 15
<211> LENGTH: 29
<212> TYPE: DNA
<213> ORGANISM: Artificial
<220> FEATURE:
<223> OTHER INFORMATION: oligonucleotide primer No 4 for Arabidopsis
      thaliana

<400> SEQUENCE: 15
aagctttatc ggtaaaacaa cgagcagag                                          29

<210> SEQ ID NO 16
<211> LENGTH: 47
<212> TYPE: DNA
<213> ORGANISM: Artificial
<220> FEATURE:
<223> OTHER INFORMATION: oligonucleotide primer No 5 for Arabidopsis
      thaliana

<400> SEQUENCE: 16
gggggtcgac gatatcacta caatgtcgga gagacaaggc tgcgcca                      47

<210> SEQ ID NO 17
<211> LENGTH: 57
<212> TYPE: DNA
<213> ORGANISM: Artificial
<220> FEATURE:
<223> OTHER INFORMATION: oligonucleotide primer No 6 for Arabidopsis
      thaliana

<400> SEQUENCE: 17
gctaaagagg tggtggccat tgtgtatgt tctgtagtga tgagttttgg tttgagt            57

<210> SEQ ID NO 18
<211> LENGTH: 45
<212> TYPE: DNA
<213> ORGANISM: Artificial
<220> FEATURE:
<223> OTHER INFORMATION: oligonucleotide primer No 7 for Arabidopsis
      thaliana

<400> SEQUENCE: 18 cccccggga agctttatcg gtaaaacaac gagcagagca agaat                         45

<210> SEQ ID NO 19
<211> LENGTH: 30
<212> TYPE: DNA
<213> ORGANISM: Artificial
<220> FEATURE:
<223> OTHER INFORMATION: oligonucleotide primer No 8 for Arabidopsis
      thaliana

<400> SEQUENCE: 19
atggccacca cctctttagc ttccgctttc                                         30

<210> SEQ ID NO 20
<211> LENGTH: 60
<212> TYPE: DNA
<213> ORGANISM: Artificial
<220> FEATURE:
<223> OTHER INFORMATION: oligonucleotide primer No 9 for Arabidopsis
      thaliana -continued

<400> SEQUENCE: 20
ggtagcttcg gcttcggctt ccactctaga ttggtccact gcttctcagc agccgaaaag    60

<210> SEQ ID NO 21
<211> LENGTH: 30
<212> TYPE: DNA
<213> ORGANISM: Artificial
<220> FEATURE:
<223> OTHER INFORMATION: oligonucleotide primer No 10 for Arabidopsis
      thaliana

<400> SEQUENCE: 21
gtggaagccg aagccgaagc taccccagtt    30

<210> SEQ ID NO 22
<211> LENGTH: 53
<212> TYPE: DNA
<213> ORGANISM: Artificial
<220> FEATURE:
<223> OTHER INFORMATION: oligonucleotide primer No 11 for Arabidopsis
      thaliana

<400> SEQUENCE: 22
acaaccacac tcatatcacc gtggtataca cactttacac cctcggttct gcg    53

<210> SEQ ID NO 23
<211> LENGTH: 50
<212> TYPE: DNA
<213> ORGANISM: Artificial
<220> FEATURE:
<223> OTHER INFORMATION: oligonucleotide primer No 12 for Arabidopsis
      thaliana

<400> SEQUENCE: 23
catatgccgc ggccgcccac tagtttgtgt atgttctgta gtgatgagtt    50

<210> SEQ ID NO 24
<211> LENGTH: 49
<212> TYPE: DNA
<213> ORGANISM: Artificial
<220> FEATURE:
<223> OTHER INFORMATION: oligonucleotide primer No 13 for Arabidopsis
      thaliana

<400> SEQUENCE: 24
actagtgggc ggccgcggca tatggtgtgt ataccacggt gatatgagt    49

<210> SEQ ID NO 25
<211> LENGTH: 34
<212> TYPE: DNA
<213> ORGANISM: Artificial
<220> FEATURE:
<223> OTHER INFORMATION: oligonucleotide primer No 14 for Arabidopsis
      thaliana

<400> SEQUENCE: 25
gcggccgcat ggccaccacc tctttagctt ccgc    34

<210> SEQ ID NO 26
<211> LENGTH: 40
<212> TYPE: DNA
<213> ORGANISM: Artificial
<220> FEATURE:
<223> OTHER INFORMATION: oligonucleotide primer No 15 for Arabidopsis
      thaliana

<400> SEQUENCE: 26
atagtttagc ggccgctgca gcttctaaaa agtatcctca           40

<210> SEQ ID NO 27
<211> LENGTH: 382
<212> TYPE: PRT
<213> ORGANISM: Umbellularia californica

<400> SEQUENCE: 27

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380

<210> SEQ ID NO 28
<211> LENGTH: 1149
<212> TYPE: DNA
<213> ORGANISM: Umbellularia californica

<400> SEQUENCE: 28

```
atggccacca cctctttagc ttccgctttc tgctcgatga aagctgtaat gttggctcgt     60
gatggccggg gcatgaaacc caggagcagt gatttgcagc tgagggcggg aaatgcgcca    120
acctctttga agatgatcaa tgggaccaag ttcagttaca cggagagctt gaaaaggttg    180
cctgactgga gcatgctctt tgcagtgatc acaaccatct tttcggctgc tgagaagcag    240
tggaccaatc tagagtggaa gccgaagccg aagctacccc agttgcttga tgaccatttt    300
ggactgcatg ggttagtttt caggcgcacc tttgccatca gatcttatga ggtgggacct    360
gaccgctcca catctatact ggctgttatg aatcacatgc aggaggctac acttaatcat    420
gcgaagagtg tgggaattct aggagatgga ttcgggacga cgctagagat gagtaagaga    480
gatctgatgt gggttgtgag acgcacgcat gttgctgtgg aacggtaccc tacttgggt    540
gatactgtag aagtagagtg ctggattggt gcatctggaa ataatggccg gcacatgat    600
ttccttgtcc gggactgcaa acaggcgaa attcttacaa gatgtaccag cctttcggtg    660
ctgatgaata caaggacaag gaggttgtcc acaatccctg acgaagttag aggggagata    720
gggcctgcat tcattgataa tgtggctgtc aaggacgatg aaattaagaa actacagaag    780
ctcaatgaca gcactgcaga ttacatccaa ggaggtttga ctcctcgatg gaatgatttg    840
gatgtcaatc agcatgtgaa caacctcaaa tacgttgcct gggttttga ccgtcca    900
gactccatct ttgagagtca tcatatttcc agcttcactc ttgaatacag gagagagtgc    960
acgagggata gcgtgctgcg gtccctgacc actgtctctg gtggctcgtc ggaggctggg   1020
ttagtgtgcg atcacttgct ccagcttgaa ggtgggtctg aggtattgag ggcaagaaca   1080
gagtggaggc ctaagcttac cgatagtttc agagggatta gtgtgatacc cgcagaaccg   1140
agggtgtaa                                                          1149
```

<210> SEQ ID NO 29
<211> LENGTH: 45
<212> TYPE: DNA
<213> ORGANISM: Artificial
<220> FEATURE:
<223> OTHER INFORMATION: oligonucleotide primer No 1 for BTE MRR197RRH

<400> SEQUENCE: 29
cggacaagga atcatgtcg ccggccatta tttccagatg cacca                    45

<210> SEQ ID NO 30
<211> LENGTH: 30
<212> TYPE: DNA
<213> ORGANISM: Artificial
<220> FEATURE:
<223> OTHER INFORMATION: oligonucleotide primer No 2 for BTE MRR197RRH

<400> SEQUENCE: 30
cggcgacatg atttccttgt ccgggactgc                                    30

METHOD OF PRODUCING FATTY ACIDS OR LIPIDS CONTAINING FATTY ACIDS USING THIOESTERASE VARIANTS

REFERENCE TO SEQUENCE LISTING SUBMITTED ELECTRONICALLY

The content of the electronically submitted substitute sequence listing, file name 2537_0710002Sequencelisting2_ascii.txt; size 24,345 bytes; and date of creation Jun. 12, 2012, filed herewith, is incorporated herein by reference in its entirety.

TECHNICAL FIELD

The present invention relates to a method of producing fatty acids or lipids containing fatty acids using thioesterase variants. Further, the present invention relates to a transformant having a gene that encodes the thioesterase variants.

BACKGROUND ART

Fatty acids are one of the principal constituent components of lipids. The fatty acids constitute lipids such as triacylglycerol by bonding to glycerin through an ester bond in vivo, and are stored and utilized as energy sources in many animals and plants. The fatty acids and lipids stored in animals and plants are widely utilized for food or industrial use, for example, intermediate materials of foods, such as monoacylglycerol and diacylglycerol, and additives or intermediate materials for various industrial products. Further, higher alcohol derivatives that are obtained by reducing higher fatty acids having approximately 12 to 18 carbon atoms are used as surfactants. For example, alkyl sulfuric acid ester salts and alkylbenzenesulfonic acid salts are utilized as anionic surfactants, and polyoxyalkylene alkyl ethers and alkyl polyglycosides are utilized as nonionic surfactants, and these surfactants are used for detergents or disinfectants. Likewise, as other higher alcohol derivatives, alkylamine salts and mono- or dialkyl quaternary amine salts are commonly utilized as fiber treatment agents, hair conditioning agents or disinfectants, and benzalkonium type quaternary ammonium salts are commonly utilized as disinfectants or antiseptics. Furthermore, higher alcohols having approximately 18 carbon atoms are also useful as growth promoting agents for plants.

As such, fatty acids are widely used for various applications, and therefore, it has been attempted to enhance the productivity of fatty acids or lipids in vivo by using animals and plants. For example, methods of increasing the lipid content in seeds by introducing acetyl-CoA carboxylase (ACCase) (Patent Literature 1, Non-Patent Literature 1, and Patent Literature 5); methods of increasing the lipid content in seeds by introducing a yeast sn-2 acyltransferase (SLC1-1) (Patent Literature 2, Patent Literature 3 and Non-Patent Literature 2); and methods of increasing the lipid content in seeds by introducing diacylglycerol acyltransferase gene (DGAT) (Patent Literature 4 and Non-Patent literature 3), have been proposed.

CITATION LIST

Patent Literatures

Patent Literature 1: JP-A-2002-335786 ("JP-A" means unexamined published Japanese patent application)
Patent Literature 2: JP-A-11-506323
Patent Literature 3: WO 2008/076377 pamphlet
Patent Literature 4: WO 2000/036114 pamphlet
Patent Literature 5: U.S. Pat. No. 5,925,805

Non-Patent Literatures

Non-Patent Literature 1: Madoka Y, Tomizawa K, Mizoi J, Nishida I, Nagano Y, Sasaki Y., "Chloroplast transformation with modified accD operon increases acetyl-CoA carboxylase and causes extension of leaf longevity and increase in seed yield in tobacco", Plant Cell Physiol., 2002 December, 43 (12), p. 1518-1525
Non-Patent Literature 2: Zou J, Katavic V, Giblin E M, Barton D L, MacKenzie S L, Keller W A, Hu X, Taylor D C., "Modification of seed oil content and acyl composition in the brassicaceae by expression of a yeast sn-2 acyltransferase gene", Plant Cell, 1997 June, 9 (6), p. 909-923
Non-Patent Literature 3: Jako C, Kumar A, Wei Y, Zou J, Barton D L, Giblin E M, Covello P S, Taylor D C., "Seed-specific over-expression of an *Arabidopsis* cDNA encoding a diacylglycerol acyltransferase enhances seed oil content and seed weight", Plant Physiol., 2001, 126 (2), p. 861-874

SUMMARY OF INVENTION

The present invention is contemplated for providing a method of producing a fatty acid or a lipid containing a fatty acid with excellent productivity, using a thioesterase variant obtained by modifying an amino acid sequence of a wild-type thioesterase. The present invention is also contemplated for providing a transformant introduced with a thioesterase variant and has an enhanced ability to produce a fatty acid or a lipid containing a fatty acid.

The present inventors made extensive studies so as to enhance the lipid productivity in animals and plants. As a result, the inventors attempted to partially modify the amino acid sequence of the thioesterase derived from California bay laurel (*Umbellularia californica*), and they found that a transformant introduced with the thioesterase variant significantly enhances the productivity of fatty acids and lipids containing fatty acids, as compared with a transformant introduced with the wild-type thioesterase. The present invention was completed based on this finding.

The present invention relates to a method of producing a fatty acid or a lipid containing a fatty acid, using any one of thioesterase variants of the following (a) to (c):
(a) Thioesterase variant comprising an amino acid sequence in which the $231^{st}$ amino acid is substituted from threonine to lysine in the amino acid sequence set forth in SEQ ID NO: 1,
(b) Thioesterase variant comprising an amino acid sequence in which one to several amino acids other than the $231^{st}$ amino acid are deleted, substituted, inserted and/or added in the amino acid sequence of the above item (a), and having thioesterase activity, and
(c) Thioesterase variant comprising at least amino acid sequence corresponding to the $84^{th}$ to $382^{nd}$ amino acids of the amino acid sequence set forth in SEQ ID NO: 1 in the amino acid sequence of the above item (a) or item (b), and having thioesterase activity.

The present invention also relates to a method of enhancing productivity of a lipid containing a fatty acid, comprising:
introducing a gene that encodes any one of thioesterase variants of the above item (a) to (c) into a host, and thereby obtaining a transformant having an enhanced ability to produce a fatty acid or a lipid containing a fatty acid.

Further, the present invention relates to a transformant having an enhanced ability to produce a fatty acid or a lipid containing a fatty acid, obtained by introducing a gene that encodes any one of thioesterase variants of the above item (a) to (c) into a host.

The present invention provides a production method of fatty acids or lipids containing fatty acids, using thioesterase variants with excellent productivity. The present invention also provides a transformant introduced with the thioesterase variant, which transformant has an enhanced ability to produce fatty acids or lipids containing fatty acids. The production method and the transformant of the present invention can be preferably used for the industrial production of fatty acids and lipids.

Other and further features and advantages of the invention will appear more fully from the following description, taken in connection with the accompanying drawings.

MODE FOR CARRYING OUT THE INVENTION

Figure 1:
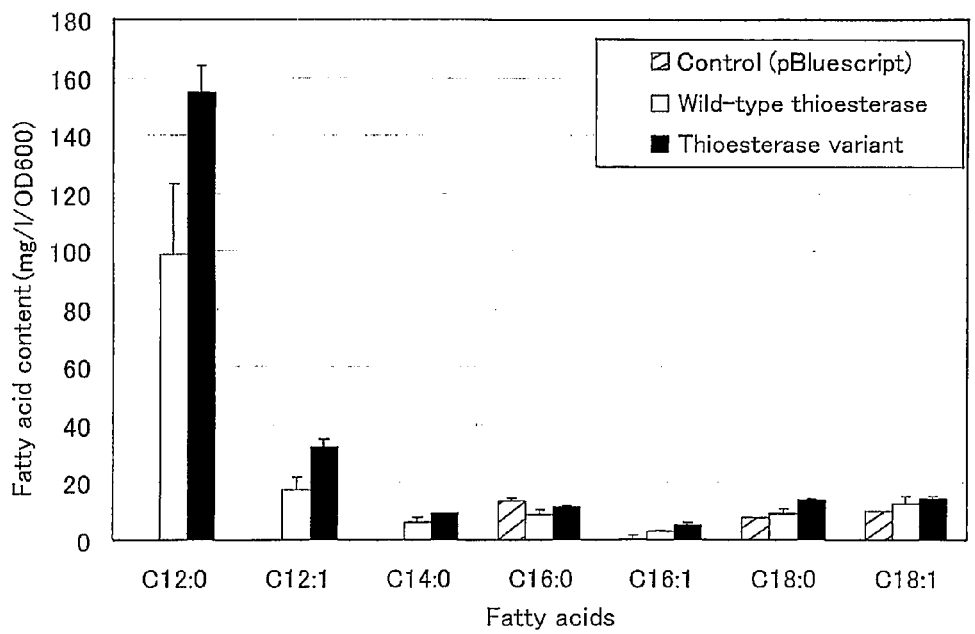
FIG. 1 is a diagram showing the contents of the individual fatty acids in transformed *Escherichia coli* cells introduced with the wild-type thioesterase gene or the thioesterase variant gene. Meanwhile, the bars shown in the diagram represent the standard deviations of triplicate experiments.

The method of producing fatty acids or lipids containing fatty acids of the present invention uses any one of thioesterase variants of the following (a) to (c). The thioesterase variants are useful for the production of fatty acids or lipids, and can significantly enhance the productivity of fatty acids and lipids containing fatty acids as compared with the wild-type thioesterase.

1. Thioesterase Variant

In the present invention, the following thioesterase variants (a) to (c) are used.

(a) Thioesterase variant comprising an amino acid sequence in which the $231^{st}$ amino acid is substituted from threonine to lysine in the amino acid sequence set forth in SEQ ID NO: 1 (that is, thioesterase variant comprising an amino acid sequence set forth in SEQ ID NO: 3)

A first embodiment of the thioesterase variant used in the present invention is a thioesterase variant comprising an amino acid sequence equivalent to the amino acid sequence set forth in SEQ ID NO: 1, except that the amino acid at $231^{st}$ position in said SEQ ID NO: 1 is substituted from threonine (Thr) to lysine (Lys). The amino acid sequence set forth in SEQ ID NO: 1 is the amino acid sequence of the thioesterase derived from California bay laurel (*Umbellularia californica*, also called California bay) (hereinafter, may be simply called the wild-type thioesterase, and is abbreviated to BTE). The thioesterase variant in which the $231^{st}$ amino acid is substituted from threonine to lysine in the wild-type thioesterase set forth in SEQ ID NO: 1, exhibits an activity of hydrolyzing a thioester bond of a acyl-acyl carrier protein (thioesterase activity).

(b) Thioesterase variant comprising an amino acid sequence in which one to several amino acids other than the $231^{st}$ amino acid are deleted, substituted, inserted and/or added in the amino acid sequence of the above item (a), and having thioesterase activity A second embodiment of the thioesterase variant used in the present invention is a thioesterase variant comprising an amino acid sequence equivalent to the amino acid sequence set forth in SEQ ID NO: 1, except that the amino acid at $231^{st}$ position in said SEQ ID NO: 1 is substituted from threonine to lysine, and further one to several amino acids other than such $231^{st}$ amino acid are deleted, substituted, inserted, and/or added in said SEQ ID NO: 1, and having thioesterase activity. In amino acid sequences encoding enzyme proteins, it is not necessarily that the complete sequence is conserved for enzyme activities, but it is known that some regions do not affect the enzyme activity even if the amino acid sequence thereof is changed. In such a region that is not essential to the enzyme activity, the enzyme activity can be maintained even if some variations such as deletions, substitutions, insertions or additions are introduced into the amino acid of the region. Likewise, the present invention can be used the variants in which the amino acid sequences are partially changed by deletions and the like while keeping the thioesterase activity.

In this case, the number of amino acids that are deleted, substituted, inserted and/or added is preferably 1 to 10, more preferably 1 to 5, and particularly preferably 1 to 2.

The thioesterase variant is more preferably a variant which has thioesterase activity and comprises an amino acid sequence in which the $231^{st}$ amino acid is substituted from threonine to lysine in the amino acid sequence set forth in SEQ ID NO: 1, and further in which the amino acids at the specific positions in the amino acid sequence set froth in SEQ ID NO: 1 are conserved as follows: the $113^{th}$ amino acid is valine or isoleucine; the $114^{th}$ amino acid is arginine; the $117^{th}$ amino acid is glutamic acid; the $118^{th}$ amino acid is valine or isoleucine; the $134^{th}$ amino acid is glutamine or arginine; the $135^{th}$ amino acid is glutamic acid or aspartic acid; the $136^{th}$ amino acid is threonine or alanine; the $145^{th}$ amino acid is glycine; the $154^{th}$ amino acid is threonine or alanine; the $162^{nd}$ amino acid is leucine; the $163^{rd}$ amino acid is isoleucine, phenylalanine or methionine; the $165^{th}$ amino acid is valine; the $176^{th}$ amino acid is tyrosine or histidine; the $177^{th}$ amino acid is proline; the $179^{th}$ amino acid is tryptophan; the $181^{st}$ amino acid is glutamic acid, aspartic acid or asparagine; the $185^{th}$ amino acid is isoleucine, valine or methionine; the $201^{st}$ amino acid is tryptophan or phenylalanine; the $215^{th}$ amino acid is alanine or cysteine; the $216^{th}$ amino acid is serine or threonine; the $217^{th}$ amino acid is serine; the $222^{nd}$ amino acid is methionine; the $226^{th}$ amino acid is threonine; the $227^{th}$ amino acid is arginine or lysine; the $229^{th}$ amino acid is leucine, phenylalanine or isoleucine; the $239^{th}$ amino acid is glutamic acid or lysine; the $257^{th}$ amino acid is lysine or arginine; the $260^{th}$ amino acid is lysine, arginine or histidine; the $300^{th}$ amino acid is proline; the $309^{th}$ amino acid is leucine or isoleucine; the $314^{th}$ amino acid is leucine, methionine or valine; the $315^{th}$ amino acid is glutamic acid or aspartic acid, the $316^{th}$ amino acid is tyrosine; the $317^{th}$ amino acid is arginine or lysine, the $318^{th}$ amino acid is arginine or lysine; and the $319^{th}$ amino acid is glutamic acid. Furthermore, a variant comprising an amino acid sequence in which one to several amino acids other than the positions mentioned above are deleted, substituted, inserted, and/or added in the amino acid sequence set forth in SEQ ID NO: 1, and having thioesterase activity, is also preferable. In this case, the number of amino acid that are deleted, substituted, inserted, and/or added is preferably 1 to 10, more preferably 1 to 5, and particularly preferably 1 to 2.

Particularly, it is preferable to use a variant which has thioesterase activity and comprises an amino acid sequence in which the $231^{st}$ amino acid is substituted from threonine to lysine in the amino acid sequence set forth in SEQ ID NO: 1, and in which the amino acids corresponding to $84^{th}$ to $230^{th}$ amino acids and $232^{nd}$ to $382^{nd}$ amino acids are conserved in said SEQ ID NO: 1. Furthermore, a variant comprising an amino acid sequence in which one to several amino acids other than the positions mentioned above are deleted, substituted, inserted, and/or added in the amino acid sequence set forth in SEQ ID NO: 1, and having thioesterase activity, is also preferable. In this case, the number of the amino acids that are deleted, substituted, inserted, and/or added is preferably 1 to 10, more preferably 1 to 5, and particularly preferably 1 to 2.

(c) Thioesterase variant comprising at least amino acid sequence corresponding to the $84^{th}$ to $382^{nd}$ amino acids of the amino acid sequence set forth in SEQ ID NO: 1 in the amino acid sequence of the above item (a) or item (b), and having thioesterase activity A third embodiment of the thioesterase variant used in the present invention is the variant of the above item (c). The variant is a particularly preferred embodiment in the present invention.

In regard to the amino acid sequence of the wild-type thioesterase set forth in SEQ ID NO: 1, it is understood that the region from the $84^{th}$ amino acid to the $382^{nd}$ amino acid is particularly important sequence for the function of thioesterase, and such region is necessary and sufficient for the protein to exhibit thioesterase activity (see Voelker, T. A., A. C. Worrell, L. Anderson, J. Bleibaum, C. Fan, D. H. Hawkins, S. E. Radke, and H. M. Davies, "Fatty acid biosynthesis redirected to medium chains in transgenic oilseed plants," Science, 1992, 257, p. 72-74). That is, a protein comprising at least amino acid sequence corresponding to the $84^{th}$ to $382^{nd}$ amino acids in the amino acid sequence set forth in SEQ ID NO: 1 can exhibit thioesterase activity. Accordingly, a protein comprising at least amino acid sequence corresponding to the $84^{th}$ to $382^{nd}$ amino acids of the amino acid sequence set forth in SEQ ID NO: 1 in the amino acid sequence of the above item (a) or (b), can also be used as the thioesterase variant in the present invention.

Hereinafter, the thioesterase variants of the above items (a) to (c) used in the present invention will be collectively referred to as the thioesterase variant, and will also be abbreviated to BTE(T231K).

The thioesterase in the present invention is an acyl-acyl carrier protein (Acyl-ACP) thioesterase which is an enzyme involved in the triglyceride biosynthesis system. The thioesterase hydrolyzes a thioester bond of an acyl-acyl carrier protein to form free fatty acids. The acyl-acyl carrier protein is a composite composed of an acyl group as a fatty acid residue and an acyl carrier protein, and is an intermediate in the process of fatty acid biosynthesis in chloroplasts or in plastids. The thioesterase acts and completes the fatty acid synthesis on the acyl carrier protein to generate free fatty acids, and then the free fatty acids are transported from the plastids and supplied to the triglyceride synthesis. Some thioesterase exhibit different reaction specificity depending on the type of the fatty acid residue constituting the substrate acyl-acyl carrier protein. Thus, it is understood that the thioesterase is an important factor in determining the fatty acid composition in an organism.

The wild-type thioesterase having the amino acid sequence set forth in SEQ ID NO: 1 has particularly high specificity to a substrate having a lauric acid (12:0) residue in an acyl group. It has been reported that when the wild-type thioesterase is introduced into *Escherichia coli* or *Arabidopsis thaliana* and thereby transforming these hosts, and as a result, lauric acids are accumulated in the transformant (Journal of Bacteriology, Vol. 176, No. 23, p. 7320-7327, 1994; and JP-A-7-501924). Further, it has been reported that, in an enzyme variant in which the $197^{th}$ amino acid is substituted from methionine to arginine, the $199^{th}$ amino acid is substituted from arginine to histidine, and the $231^{st}$ amino acid is substituted from threonine to lysine in the amino acid sequence of the wild-type thioesterase set forth in SEQ ID NO: 1, the substrate showing particularly-high specificity changes from a fatty acid having 12 carbon atoms (C12:0) to a fatty acid having 14 carbon atoms (C14:0) (Proc. Natl. Acad. Sci. USA, Vol. 92, pp. 10639-10643, 1995). Furthermore, this Literature describes that an enzyme variant in which only the $231^{st}$ amino acid is singly substituted from threonine to lysine, does not exhibit any change in the substrate specificity.

However, there has been no report that thioesterase variants obtained by modifying the amino acid sequence of the wild-type thioesterase enhance the productivity of fatty acids and lipids containing fatty acids in an organism, as compared with the wild-type thioesterase, and this is new findings obtained by the inventors of the present invention.

The method of obtaining the thioesterase variant used in the present invention is not particularly limited, and the thioesterase variant can be obtained by conventional genetic engineering techniques. For example, the amino acid sequence data or the nucleotide sequence data of the wild-type thioesterase may be obtained, and based on these data, the amino acid sequence or nucleotide sequence at a desired position can be subjected to substitution (variation) by a technique such as a site-specific mutagenesis method.

The amino acid sequence of the wild-type thioesterase (SEQ ID NO: 1) and the nucleotide sequence encoding the amino acid sequence (for example, SEQ ID NO: 2) can be obtained from databases such as GenBank (for example, according to GenBank, protein sequence: AAA34215.1, mRNA sequence: M94159.1). Based on the sequence thus obtained, a gene that encodes the wild-type thioesterase can be obtained by artificial synthesis. The artificial synthesis of a gene can be achieved by utilizing the services such as Invitrogen, Inc. Furthermore, a gene that encodes the wild-type thioesterase can also be obtained by cloning from California bay laurel, and the cloning can be carried out by, for example, the methods described in Molecular Cloning—A LABORATORY MANUAL THIRD EDITION [Joseph Sambrook, David W. Russell, Cold Spring Harbor Laboratory Press (2001)] and the like.

Examples of the method for introducing site-specific variation include a method of utilizing the splicing overlap extension (SOE) PCR (Horton et al., Gene 77, 61-68, 1989) used in the Example section that will be described below; the ODA method (Hashimoto-Gotoh et al., Gene, 152, 271-276, 1995);

and the Kunkel method (Kunkel, T. A., Proc. Natl. Acad. Sci. USA, 1985, 82, 488). Furthermore, commercially available kits such as the Site-Directed Mutagenesis System Mutan-SuperExpress Km kit (Takara Bio, Inc.), the Transformer TM Site-Directed Mutagenesis kit (Clonetech Laboratories, Inc.), and the KOD-Plus-Mutagenesis kit (Toyobo Co., Ltd.) can also be utilized. Among these, according to the present invention, it is preferable to carry out the introduction of site-specific variation according to the SOE-PCR method.

An example of specific method for preparing a gene that encodes the thioesterase variant used in the present invention is shown as follows: First, an artificially synthesized nucleotide sequence of the wild-type thioesterase gene (for example, the nucleotide sequence set forth in SEQ ID NO: 2) is treated with a restriction enzyme and is incorporated into a vector. Next, two kinds of DNA fragments are amplified by PCR using the vector DNA thus obtained as a template, and primers. As one of the primers, for example, an oligonucleotide including a nucleotide sequence that encodes the amino acid sequence in which $231^{st}$ threonine is substituted to lysine in the amino acid sequence set forth in SEQ ID NO: 1 (for example, an oligonucleotide having the nucleotide sequence set forth in SEQ ID NO: 7 or 8), can be used. As the other primer, an oligonucleotide including a nucleotide sequence near each of two terminal regions of the wild-type thioesterase gene (for example, an oligonucleotide having the nucleotide sequence set forth in SEQ ID NO: 5 or 6), can be used. Subsequently, a DNA fragment having a nucleotide sequence corresponding to the amino acid sequence set forth in SEQ ID NO: 3 (for example, SEQ ID NO: 4) can be obtained by splicing overlap extension (SOE) PCR using the two kinds of DNA fragments thus obtained as templates, and the oligonucleotide primer including a nucleotide sequence near each of two terminal regions of the wild-type thioesterase gene (for example, an oligonucleotide having a nucleotide sequence set forth in SEQ ID NO: 5 or 6). A preferred example of the reaction conditions for PCR as follows: a thermal denaturation reaction of making a double-stranded DNA into single strands is carried out at 94° C. for 30 seconds; an annealing reaction of hybridizing a primer pair with the single-stranded DNA is carried out at 55° C. for about 30 seconds; an elongation reaction of operating a DNA polymerase is carried out at 72° C. for about 70 seconds; and a process consisting of these three reactions as one cycle is carried out in 30 cycles.

2. Transformant

Another embodiment of the present invention can provide a transformant which is obtained by introducing a gene that encodes any one of the thioesterase variants of the above items (a) to (c) into a host, and which has an enhanced ability to produce fatty acids or lipids containing fatty acids. The transformant of the present invention having a gene encoding the thioesterase variant exhibits a significantly enhanced ability to produce fatty acids or lipids containing fatty acids, as compared with a transformant having the wild-type thioesterase gene. In the present invention, the ability to produce fatty acids and lipids containing fatty acids of the wild-type thioesterase or the thioesterase variant can be measured by the method used in the Examples.

The transformant of the present invention is obtained by introducing a gene that encodes the thioesterase variant into a host according to a conventional genetic engineering method. Specifically, the transformant can be produced by preparing a vector which is capable of expressing a gene that encodes the thioesterase variant in a host cell, introducing this vector into host cells, and thereby transforming the host cells. Subsequently, the transformant thus obtained is cultured under suitable conditions, and fatty acids and lipids containing fatty acids can be produced in the transformant.

A nucleotide sequence of a gene that encodes the thioesterase variant can be obtained by a conventional method from the amino acid sequence of any one of the thioesterase variants of (a) to (c) described above. Specific examples of the nucleotide sequence of a gene encoding the thioesterase variant include nucleotide sequences of the following (d) to (f), but are not intended to be limited to these.

(d) A nucleotide sequence in which the $691^{st}$ to $693^{rd}$ nucleotides encoding threonine are substituted by nucleotides encoding lysine in the nucleotide sequence set forth in SEQ ID NO: 2 (for example, the nucleotide sequence set forth in SEQ ID NO: 4).

(e) A nucleotide sequence in which one to several nucleotides, other than the $691^{st}$ to $693^{rd}$ nucleotides, are deleted, substituted, inserted, and/or added in the nucleotide sequence of the above item (d); and the protein encoded by a DNA consisting of the above nucleotide sequence has thioesterase activity. Meanwhile, the positions and number of the nucleotides that are deleted, substituted, inserted, and/or added can be appropriately designed so as to maintain thioesterase activity, by making reference to the conserved region of the amino acid sequence as shown in the thioesterase variant of the above item (b).

(f) A nucleotide sequence including at least nucleotide sequence corresponding to the $250^{th}$ to $1149^{th}$ nucleotides of the nucleotide sequence set forth in SEQ ID NO: 2 in the nucleotide sequence of the above item (d) or (e).

The host for the transformant is not particularly limited, and a microorganism, a plant or an animal can be used. Even an organism which inherently does not have a thioesterase that recognizes a fatty acid residue having 12 carbon atoms as a substrate, can also be used as the host. According to the present invention, it is preferable to use a microorganism and a plant as the host, from the viewpoints of production efficiency and the usability of fatty acids and lipids thus obtained. As the microorganism, prokaryotes such as microorganisms which belong to the genus *Escherichia* or microorganisms which belong to the genus *Bacillus*; or eukaryotes such as yeast or filamentous fungi can be used. Among them, *Escherichia coli, Bacillus subtilis, Rhodosporidium toruloides*, and *Mortierella* sp. are preferred, and *Escherichia coli* is particularly preferred. As the plant, *Arabidopsis thaliana*, rapeseed, coconut, palm, cuphea, and yatropha are preferred, and *Arabidopsis thaliana* is particularly preferred.

The vector used may be any vector capable of introducing a gene that encodes the thioesterase variant into a host, and expressing the gene in the host cells. For example, an expression vector which has expression regulation regions such as a promoter and a terminator in accordance with the type of the host to be used, and has a replication initiation point, a selection marker or the like, can be used. Furthermore, the vector may also be a vector which is capable of self-proliferation and self-replication outside the chromosome, such as a plasmid, or may also be a vector which is incorporated into the chromosome.

Specific examples of the vector include, in the case of using a microorganism as the host, pBluescript II SK(-) (manufactured by Stratagene Corp.), pUC119 (manufactured by Takara Shuzo Co., Ltd.), a pET-based vector (manufactured by Takara Bio, Inc.), a pGEX-based vector (manufactured by GE Healthcare, Inc.), a pCold-based vector (manufactured by Takara Bio, Inc.), pHY300PLK (manufactured by Takara Bio, Inc.), pUB110 (Mckenzie, T. et al., (1986), Plasmid 15(2); p. 93-103), pBR322 (manufactured by Takara Bio, Inc.), pRS403 (manufactured by Stratagene Corp.), and pMW218/219 (manufactured by Nippon Gene Co., Ltd.). In the case of using a plant cell as the host, examples of the vector include a pRI-based vector (manufactured by Takara Bio, Inc.), a pBI-based vector (manufactured by Clontech Laboratories, Inc.), and an IN3-based vector (manufactured by Inplanta Innovations, Inc.). Particularly, in the case of using *Escherichia coli* as the host, pBluescript II SK(-) (manufactured by Stratagene Corp.) and pMW218/219 (manufactured by Nippon Gene Co., Ltd.) are used preferably. In the case of using *Arabidopsis thaliana* as the host, a pRI-based vector (manufactured by Takara Bio, Inc.) and a pBI-based vector (manufactured by Clontech Laboratories, Inc.) are used preferably.

The expression regulation regions such as a promoter and a terminator, and the selection marker are not particularly limited, and can be appropriately selected from conventionally used promoters, markers and the like in accordance with the type of the host to be used. Specific examples of the promoter include lac promoter, trp promoter, tac promoter, trc promoter, T7 promoter, SpoVG promoter, cauliflower mosaic virus 35S RNA promoter, promoters for housekeeping genes such as actin and ubiquitin, rapeseed-derived Napin gene promoter, and plant-derived Rubisco promoter. Examples of the selection marker include drug resistance genes such as antibiotic resistance genes (ampicillin resistance gene, chloramphenicol resistance gene, erythromycin resistance gene, neomycin resistance gene, kanamycin resistance gene, spectinomycin resistance gene, tetracycline resistance gene, blasticidin S resistance gene, bialaphos resistance gene, and hygromycin resistance gene). Further, it is also possible to use a deletion of an auxotrophy-related gene or the like as a selection marker.

A vector for transformation can be constructed by introducing a gene encoding the thioesterase variant into the above-described vector according to a conventional technique such as restriction enzyme treatment or ligation.

The method for transformation is not particularly limited as long as it is a method capable of introducing a target gene into a host. For example, a method of using calcium ion, a general competent cell transformation method (J. Bacterial. 93, 1925 (1967)), a protoplast transformation method (Mol. Gen. Genet. 168, 111 (1979)), an electroporation method (FEMS Microbiol. Lett. 55, 135 (1990)), an LP transformation method (T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829) and the like, can be used.

Further, the selection of a transformant having a target gene fragment introduced therein can be carried out by using a selection marker or the like. For example, the selection can be carried out by using an indicator whether a transformant is acquired the drug resistance as a result of introducing a vector-derived drug resistance gene into a host cell together with a target DNA fragment. Further, the introduction of a target DNA fragment can also be confirmed by PCR using a genome as a template.

3. Method of Producing Fatty Acid and Lipid Containing Fatty Acid

The method of producing fatty acids or lipids containing fatty acids of the present invention uses the thioesterase variant described above. Specifically, a method of using a transformant containing a gene that encodes a thioesterase variant, and a method of performing the excision of a fatty acid from Acyl-ACP in vitro using a purified Acyl-ACP and the thioesterase variant to produce fatty acids or lipids (Yuan et al., PNAS, 1995, (92), p. 10639-10643), can be used.

The production method of the present invention is preferably a method comprising: using a transformant raving a gene that encodes the thioesterase variant, producing fatty acids or lipids containing fatty acids in the transformant, and collecting the resulting fatty acids or lipids. More specifically, the method of the present invention is preferably a method comprising: obtaining a transformant (recombinant) having a gene that encodes the thioesterase variant introduced therein as described above, and subsequently culturing and growing the transformant under appropriate conditions, and collecting fatty acids or lipids containing fatty acids from the culture or the transformant.

The conditions for culture and growth of a transformant can be selected in accordance with the type of the host having a gene introduced therein, and any appropriate preferred conditions can be employed. For instance, in the case of using *Escherichia coli* as the host for transformation, culture may be carried out in LB medium at 30° C. to 37° C. for half a day to 1 day. In the case of a using *Arabidopsis thaliana* as the host for transformation, growth may be carried out under the temperature conditions of 20° C. to 25° C., by continuously irradiating white light or under the illumination conditions of a light period of 16 hours and a dark period of 8 hours, for one to two months.

From the viewpoint of the production efficiency of fatty acids and lipids, substrates for thioesterase or precursor substances participating in the fatty acid biosynthesis system, such as glycerol, acetic acid, malonic acid and the like, may be added to the medium.

After fatty acids or lipids are produced by culturing and growing a transformant, these fatty acids and lipids containing fatty acids are collected from the culture or the transformant by performing isolation, purification and the like.

The method of isolating and collecting fatty acids or lipids containing fatty acids produced in a transformant are not particularly limited, and the conventional method that are used to isolate lipid components and the like from organisms may be used. For example, fatty acids or lipids containing fatty acids can be isolated and collected from a culture or a transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from a culture or a transformant through pressing or extraction, and then performing general purification processes such as degumming, deacidification, decoloration, dewaxing, and deodorization. After lipid components containing fatty acids are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

In the above-described manner, fatty acids or lipids containing fatty acids can be produced by using the thioesterase variant. The production method of the present invention can be preferably used in the production of long-chain fatty acids having 12 or more carbon atoms or lipids containing these fatty acids, more preferably used in the production of fatty acids having 12 to 18 carbon atoms or lipids containing these fatty acids, still more preferably used in the production of fatty acids having 12 to 14 carbon atoms or lipids containing these fatty acids, particularly preferably used in the production of lauric acid or lipids containing the lauric acid.

The fatty acids or lipids obtained by the production method and the transformant of the present invention can be utilized for food, as well as can be utilized as an emulsifier incorporated into cosmetic products or the like, a cleansing agent such as a soap or a detergent, a fiber treatment agent, a hair conditioning agent, a disinfectant or an antiseptic.

EXAMPLES

Hereinafter, the present invention will be described more in detail with reference to Examples, but the present invention is not limited thereto.

Example 1

Construction of Transformant By Introducing Thioesterase Variant (BTE(T231K)) Gene into *Escherichia coli*, and Production of Fatty Acids and Lipids in Transformant 1. Construction of Wild-Type Thioesterase (BTE) Gene Expression Plasmid A DNA fragment of the wild-type thioesterase gene was amplified by PCR using a gene that encodes the wild-type thioesterase set forth in SEQ ID NO: 2 as a template, and using a pair of primers set forth in SEQ ID NO: 5 and SEQ ID NO: 6 as shown in the following Table 1. The gene having the nucleotide sequence set forth in SEQ ID NO: 2 was obtained by utilizing the custom synthesis service provided by Invitrogen, Inc. The wild-type thioesterase gene fragment obtained by PCR was digested with restriction enzyme Xba I. Further, plasmid vector pBluescriptII SK(−) (Stratagene Corp., San Diego, Calif.) was also digested with Xba I, and then was subjected to dephosphorylation treatment. These two restriction enzyme digestion products were linked by ligation, and the wild-type thioesterase gene fragment (nucleotide sequence corresponding to the $249^{th}$ to $1149^{th}$ nucleotides of the nucleotide sequence set forth in SEQ ID NO: 2) was inserted into Xba I site of the pBluescriptII SK(−). As a result, a plasmid which expresses the wild-type thioesterase in the form of being fused to the $27^{th}$ amino acid on the N-terminal side of the vector-derived LacZ protein, was constructed. The insertion of the gene encoding the wild-type thioesterase into the plasmid was confirmed by DNA sequencing.

2. Construction of Thioesterase Variant (BTE(T231K)) Gene Expression Plasmid

The wild-type thioesterase expression plasmid constructed in the above section 1 was used as a template, two kinds of gene fragments were amplified by PCR using a pair of primers set forth in SEQ ID NO: 5 and SEQ ID NO: 8, or a pair of primers set forth in SEQ ID NO: 6 and SEQ ID NO: 7 as shown in the following Table 1, The obtained two kinds of fragments were used as templates, splicing overlap extension (SOE) PCR (Horton et al., Gene, 77, 61-68, 1989) was carried out with the pair of primers set forth in SEQ ID NO: 5 and SEQ ID NO: 6. As a result, a DNA fragment of a thioesterase variant gene in which the nucleotide sequence ACA (Thr) was substituted by AAG (Lys) at the 691 to 693 positions in the wild-type thioesterase set forth in SEQ ID NO: 2, was obtained. The DNA fragment of the thioesterase variant gene thus obtained was digested with restriction enzyme Xba I. Further, plasmid vector pBluescriptII SK(−) (Stratagene Corp.) was also digested with Xba I, and then was subjected to dephosphorylation treatment. These two digestion products were linked by ligation, and the thioesterase variant gene fragment (nucleotide sequence corresponding to the $249^{th}$ to $1149^{th}$ nucleotides of the nucleotide sequence set forth in SEQ ID NO: 4) was inserted into Xba I site of the pBluescriptII SK(−). As a result, a plasmid which expresses the thioesterase variant in the form of being fused to the $27^{th}$ amino acid on the N-terminal side of the vector-derived LacZ protein, was constructed. The insertion of the gene encoding the thioesterase variant into the plasmid was confirmed by DNA sequencing.

TABLE 1

| | Primer sequence |
|---|---|
| SEQ ID NO: 5 | GGAAAAGGTGGTGAACTACTATGTCTAGAGTGGAAGCCGAAGC |
| SEQ ID NO: 6 | TTAATCTAGACTGCAGCTTCTAAAAAG |
| SEQ ID NO: 7 | AAGATCCCTGACGAAGTTAGAGGGGAGATAG |
| SEQ ID NO: 8 | CTCTAACTTCGTCAGGGATCTTGGACAACCTCCTTGTCCTT |

3. Construction of Transformant Having Wild-Type Thioesterase (BTE) Gene or Thioesterase Variant (BTE (T231K)) Gene An *Escherichia coli* mutant strain, strain K27 (fadD88) (Overath et al, Eur. J. Biochem. 7, 559-574, 1969), was transformed by a competent cell transformation method, using the plasmid that express the wild-type thioesterase or the plasmid that express the thioesterase variant constructed in the above sections 1 and 2. The transformed strain K27 was left to stand overnight at 30° C., and those colonies thus obtained were inoculated in 1 mL of LBAmp liquid medium (Bacto Trypton 1%, yeast extract 0.5%, NaCl 1%, and ampicillin sodium 50 μg/mL), and was subjected to shaking culture for 12 hours at 30° C. After 12 hours, 25 μL of the culture fluid was added to another 2.5 mL of LBAmp liquid medium, and the mixture was subjected to shaking culture at 30° C. After a lapse of 15 hours from the initiation of culture, lipid components contained in the culture fluid were analyzed by the method described below. Further, after a lapse of 15 hours from the initiation of culture, the light absorbance at 600 nm (OD600) of the culture fluid was measured to calculate the cell numbers of *Escherichia coli* contained in the culture fluid. As a negative control, *Escherichia coli* strain K27 that was transformed with plasmid vector pBluescriptII SK(−), was also subjected to the same experiment.

4. Extraction of Lipid in *Escherichia coli* Culture Fluid and Analysis of Fatty Acid Contained Therein To 900 μL of the culture fluid obtained after a lapse of 15 hours from the initiation of culture, 40 μL of acetic acid, and 40 µL of 7-pentadecanone (0.5 mg/mL) dissolved in methanol as an internal standard were added. To this liquid, 0.5 mL of chloroform and 1 mL of methanol were added, and the mixture was sufficiently stirred and then was left to stand for 15 minutes. Further, 0.5 mL of a 1.5% aqueous solution of potassium chloride and 0.5 mL of chloroform were added thereto, and the mixture was sufficiently stirred and then was left to stand for 15 minutes. The mixture was centrifuged for 5 minutes at room temperature and at 1,500 rpm, and then the lower layer was collected and dried with nitrogen gas. 1 mL of a boron trifluoride-methanol complex solution was added to the dried sample, and the mixture was kept warm at 80° C. for 10 minutes to thereby performing methyl esterification treatment of fatty acids. Thereafter, 1 mL of saturated brine and 1 mL of hexane were added thereto, and the mixture was sufficiently stirred and then was left to stand for 30 minutes. The upper layer was collected and provided for gas chromatographic analysis (Hewlett Packard 6890). The gas chromatography was carried out under the conditions as follows: [capillary column: DB-1 MS 30 m×200 µm×0.25 µm (J&W Scientific, Inc.), mobile layer: high purity helium, flow rate inside the column: 1.0 mL/min, temperature rise program: 100° C. (for 1 min)→10° C./min→300° C. (for 5 min), equilibration time: for 1 min, injection port: split injection (split ratio: 100:1), pressure 14.49 psi, 104 mL/min, amount of injection 1 µL, vial cleaning: methanol chloroform, detector temperature: 300° C.].

5. Analysis of Lipid and Fatty Acid Content in *Escherichia coli* Culture Fluid

Amounts of fatty acid methyl esters were quantitatively determined based on the peak areas of the waveform data obtained by the above gas chromatographic analysis. The peak areas corresponding to the individual fatty acids were compared with that of 7-pentadecanone as the internal standard, and carried out corrections between the samples, and then the contents of the individual fatty acids per liter of the culture fluid were calculated. Further, the contents of the individual fatty acids thus calculated were normalized with respect to the cell numbers of *Escherichia coli* contained in the culture fluid previously measured (OD600). The results are shown in FIG. 1.

Furthermore, the total content of the individual fatty acids (the total lipid content) was calculated by summing the contents of the individual fatty acids thus obtained. The results are shown in FIG. 2.

As is apparent from FIG. 1, the transformant having the thioesterase variant gene exhibited an increase in the contents (amounts of production) of the individual fatty acids to a large extent, as compared with the transformant having the wild-type thioesterase gene. Specifically, the transformant having the thioesterase variant gene exhibited 1.6 times the content of lauric acid (C12:0), 1.9 times the content of lauroyl acid (C12:1), 1.4 times the content of myristic acid (C14:0), 1.3 times the content of palmitic acid (C16:0), 1.9 times the content of palmitoleic acid (C16:1), 1.6 times the content of stearic acid (C18:0), and 1.1 times the content of oleic acid (C18:1), compared with the transformant having the wild-type thioesterase gene.

Figure 2:
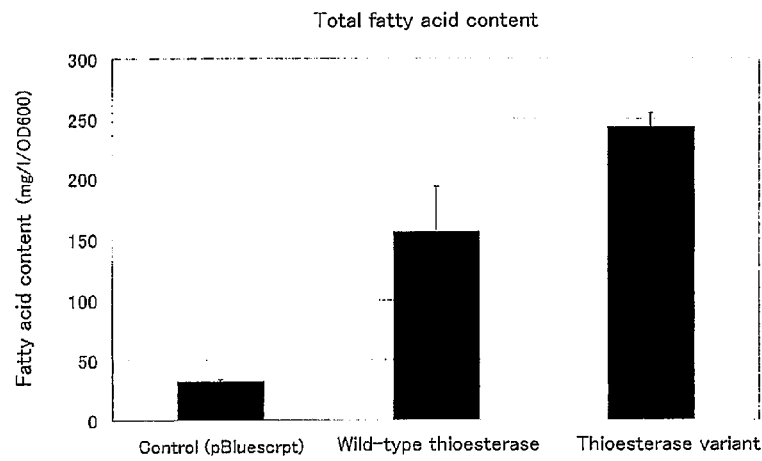
FIG. 2 is a diagram showing the total content of the individual fatty acids in transformed *Escherichia coli* cells introduced with the wild-type thioesterase gene or the thioesterase variant gene. Meanwhile, the bars shown in the diagram represent the standard deviations of triplicate experiments.

Further, as shown in FIG. 2, the total content of the individual fatty acids (the total lipid content) in the transformant having the thioesterase variant gene of the present invention, also largely increased 1.6 times compared with that of the transformant having the wild-type thioesterase gene.

Example 2

Construction of Transformant by Introducing Thioesterase Variant (BTE(T231K)) Gene into *Arabidopsis thaliana*, and Production of Fatty Acids and Lipids in Transformant 1. Cloning of Promoter Region and Terminator Region of Napin Gene A promoter region of Napin gene derived from *Brassica raga* was obtained by using a wild oilseed rape-like plant collected from Itako City, Ibaraki Prefecture, and a terminator region of Napin gene derived from *Brassica raga* was obtained by using a wild oilseed rape-like plant collected from Mashiko-cho, Tochigi Prefecture, respectively according to the following method.

Genome DNA was extracted from the plants described above using Power Plant DNA Isolation Kit (MO BIO Laboratories, USA). The genome DNA thus obtained was used as a template, the promoter and terminator regions were amplified by PCR using a DNA polymerase PrimeSTAR. Specifically, the promoter region of Napin gene derived from *Brassica rapa* was amplified by using a pair of primers set forth in SEQ ID NO: 12 and SEQ ID NO: 13 as shown in Table 2, and the terminator region of Napin gene derived from *Brassica rapa* was amplified by using a pair of primers set forth in SEQ ID NO: 14 and SEQ ID NO: 15. Further, PCR was carried out again using the PCR products of the promoter and terminator of Napin gene derived from *Brassica rapa* thus amplified, as templates. At this PCR, a pair of primers set forth in SEQ ID NO: 16 and SEQ ID NO: 17 as shown in Table 2 was used for amplifying the promoter of Napin gene, and a pair of primers set forth in SEQ ID NO: 14 and SEQ ID NO: 18 as shown in Table 2 was used for amplifying the terminator of Napin gene. The DNA fragments amplified by PCR were treated by adding deoxyadenine (dA) to the two termini using Mighty TA-cloning Kit (manufactured by Takara Bio, Inc.), subsequently the DNA fragments were respectively inserted into pMD20-T vector (manufactured by Takara Bio, Inc.) by ligation. As a result, a plasmid pPNapin1 containing the Napin gene promoter and a plasmid pTNapin1 containing the Napin gene terminator were respectively constructed. These plasmids were supplied to sequence analysis, and thus the nucleotide sequence of the promoter region (SEQ ID NO: 9) and the nucleotide sequence of the terminator region (SEQ ID NO: 10) were determined.

TABLE 2

| | Primer sequence (5'-3') |
|---|---|
| SEQ ID NO: 12 | GATATCACTACAATGTCGGAGAGACAAGGC |
| SEQ ID NO: 13 | TTGTGTATGTTCTGTAGTGATGAGTTTTGG |
| SEQ ID NO: 14 | AGTGTGTATACCACGGTGATATGAGTGT |
| SEQ ID NO: 15 | AAGCTTTATCGGTAAAACAACGAGCAGAG |
| SEQ ID NO: 16 | GGGGGTCGACGATATCACTACAATGTCGGAGAGACAAGGCTGCGCCA |

TABLE 2-continued

| | Primer sequence (5'-3') |
|---|---|
| SEQ ID NO: 17 | GCTAAAGAGGTGGTGGCCATTTGTGTATGTTCTGTAGTGATGAGTTTTGGTTTGAGT |
| SEQ ID NO: 18 | CCCCCCGGGAAGCTTTATCGGTAAAACAACGAGCAGAGCAAGAAT |
| SEQ ID NO: 19 | ATGGCCACCACCTCTTTAGCTTCCGCTTTC |
| SEQ ID NO: 20 | GGTAGCTTCGGCTTCGGCTTCCACTCTAGATTGGTCCACTGCTTCTCAGCAGCCGAAAAG |
| SEQ ID NO: 21 | GTGGAAGCCGAAGCCGAAGCTACCCCAGTT |
| SEQ ID NO: 22 | ACAACCACACTCATATCACCGTGGTATACACACTTTACACCCTCGGTTCTGCG |
| SEQ ID NO: 23 | CATATGCCGCGGCCGCCCACTAGTTTGTGTATGTTCTGTAGTGATGAGTT |
| SEQ ID NO: 24 | ACTAGTGGGCGGCCGCGGCATATGGTGTGTATACCACGGTGATATGAGT |
| SEQ ID NO: 25 | GCGGCCGCATGGCCACCACCTCTTTAGCTTCCGC |
| SEQ ID NO: 26 | ATAGTTTAGCGGCCGCTGCAGCTTCTAAAAAGTATCCTCA |

2. Cloning of Chloroplast Transit Signal Peptide and Thioesterase Gene

A gene encoding the chloroplast transit signal peptide of the Acyl-ACP thioesterase (BTE) gene derived from California bay was obtained by utilizing the custom synthesis service provided by Invitrogen, Inc, (Carlsbad, Calif.) (SEQ ID NO: 11).

A plasmid containing a sequence of the gene obtained above was used as a template, a gene fragment of the gene that encodes the chloroplast transit signal peptide was amplified by PCR using PrimeSTAR and a pair of primers set forth in SEQ ID NO: 19 and SEQ ID NO: 20 as shown in Table 2. Further, a plasmid containing the wild-type thioesterase (BTE) gene was used as a template, a gene fragment of the BTE was amplified by PCR using PrimeSTAR and a pair of primers set forth in SEQ ID NO: 21 and SEQ ID NO: 22 as shown in Table 2. Next, the two gene fragments thus amplified were used as templates, the two gene fragments were linked by splicing overlap extension (SOE) PCR (Horton et al., Gene, 1989) using PrimeSTAR and a pair of primers set forth in SEQ ID NO: 19 and SEQ ID NO: 22 as shown in Table 2. As a result, a gene fragment corresponding to the full length of the wild-type thioesterase (BTE) gene linked with the chloroplast transit signal peptide was constructed.

Next, a gene fragment corresponding to the full length of the thioesterase variant (BTE(T231K)) gene linked with the chloroplast transit signal peptide was constructed in the same manner by using a pair of primers set forth in SEQ ID NO: 19 and SEQ ID NO: 22 as shown in Table 2.

The gene fragments thus amplified were treated by adding deoxyadenine (dA) to the two termini using Mighty TA-cloning Kit (manufactured by Takara Bio, Inc.), subsequently the gene fragments were respectively inserted into pMD20-T vector (manufactured by Takara Bio, Inc.) by ligation. As a result, a plasmid pBTEsig1 having the BTE gene inserted therein, and a plasmid pBTE(T231K)sig1 having the BTE (T231K) gene inserted therein were respectively constructed.

3. Construction of Vector for Transfection of Plant Cell

As a vector for transfection of plant cells, pRI909 (manufactured by Takara Bio, Inc.) was used.

First, the promoter and the terminator of Napin gene derived from Brassica raga were introduced into pRI909. A DNA fragment of the promoter region was amplified by PCR using PrimeSTAR with the plasmid pPNapin1 produced in the above section 1 as a template, and a pair of primers set forth in SEQ ID NO: 16 and SEQ ID NO: 23 as shown in Table 2. Further, a DNA fragment of the terminator region was amplified by PCR using PrimeSTAR with the plasmid pTNapin1 produced in the above section 1 as a template, and a pair of primers set forth in SEQ ID NO: 18 and SEQ ID NO: 24 as shown in Table 2. The amplified fragments were treated by adding deoxyadenine (dA) to the two termini using Mighty TA-cloning Kit (manufactured by Takara Bio, Inc.), subsequently the fragments were respectively inserted into pMD20-T vector (manufactured by Takara Bio, Inc.) by ligation, and thus plasmids pPNapin2 and pTNapin2 were respectively constructed. The plasmid pPNapin2 was treated with restriction enzymes Sal 1 and Not 1, and the plasmid pTNapin2 was treated with restriction enzymes Sma 1 and Not 1. The treated plasmids were inserted into pRI909 (that was previously treated with restriction enzymes Sal 1 and Sma 1) by ligation, and thus, plasmid p909PTnapin was constructed.

Next, the BTE gene or the BTE(T231K) gene was introduced to the downstream of the Napin gene promoter. The plasmid pBTEsig1 or pBTE(T231K)sig1 produced in the above section 2. was used as a template, and gene fragments were respectively amplified using PrimeSTAR and a pair of primers set forth in SEQ ID NO: 25 and SEQ ID NO: 26 as shown in Table 2. The amplified gene fragments were treated by adding deoxyadenine (dA) to the two termini using Mighty TA-cloning Kit (manufactured by Takara Bio, Inc.), subsequently the gene fragments were respectively inserted to pMD20-T vector (manufactured by Takara Bio, Inc.) by ligation, and thus plasmids pBTEsig2 and pBTE(T231K)sig2 were respectively constructed. The plasmids pBTEsig2 and p909PTnapin were respectively treated with restriction enzyme Not 1, and the digestion fragments thus obtained were linked by ligation. Thereby, a vector for transfection of plant cells: p909BTE in which the BTE gene was inserted between the Napin gene promoter and the Napin gene terminator, was constructed. In the same manner, a vector for transfection of plant cells: p909BTE(T231K) in which the BTE(T231K) gene was inserted between the Napin gene promoter and the Napin gene terminator, was constructed.

4. Method of Transformation and Growth of *Arabidopsis Thaliana*

The vectors p909BTE and p909BTE(T231K) for transfection of plant cells were supplied to the custom service for *Arabidopsis thaliana* transformation by Inplanta Innovations, Inc., and thus transformants of *Arabidopsis thaliana* (Colombia) having the BTE gene and BTE(T231K) gene respectively introduced therein: Pnapin-BTE and Pnapin-BTE(T231K) were respectively obtained.

The wild-type strain of *Arabidopsis thaliana* and the transformants Pnapin-BTE and Pnapin-BTE(T231K) were grown at room temperature of 22° C., under the conditions of a light period of 16 hours (about 4000 lux) using fluorescent lamp illumination and a dark period of 8 hours. After the cultivation for about 2 months, seeds were harvested.

5. Analysis of Lipid Contents and Fatty Acid Composition in *Arabidopsis thaliana* Seeds (1) Lipid Extraction From Seeds and Methyl Esterification of Fatty Acids Approximately two spoons of the *Arabidopsis thaliana* seeds thus harvested were scooped with a seed spoon (200-grain capacity, manufactured by Biomedical Science Co., Ltd.) and were put into Lysing Matrix D (MP Biomedicals, Inc., USA). The Lysing Matrix D was mounted on FastPrep (MP Biomedicals LLC), and the seeds were crushed by applying vibration for 20 seconds at a speed of 6.0. To the crushed seeds, 20 μL of 7-pentadecanone (0.5 mg/mL) (internal standard) dissolved in methanol and 20 μL of acetic acid were added. 0.25 mL of $CHCl_3$ and 0.5 mL of methanol were added thereto, and the mixture was sufficiently stirred and then was left to stand for 15 minutes. Further, 0.25 mL of a 1.5% aqueous solution of potassium chloride and 0.25 mL of $CHCl_3$ were added thereto, and the mixture was sufficiently stirred and then was left to stand for 15 minutes. The mixture was centrifuged for 5 minutes at room temperature and at 1,500 rpm, and then the lower layer was collected and dried with nitrogen gas. 100 μL of 0.5 N KOH dissolved in methanol was added to the dried sample, and the mixture was kept at a constant temperature of 70° C. for 30 minutes to hydrolyze triacylglycerol. The dried product was dissolved by adding 0.3 mL of a boron trifluoride-methanol complex solution, and the solution was kept at a constant temperature of 80° C. for 10 minutes to thereby carry out methyl esterification of fatty acids. Thereafter, 0.2 mL of saturated brine and 0.3 mL of hexane were added thereto, and the mixture was sufficiently stirred and then was left to stand for 30 minutes. The hexane layer (upper layer) containing methyl esters of fatty acids was collected and supplied to gas chromatographic (GC) analysis. Further, for counting the number of seeds, the seeds before being put into the Lysing matrix D were spread on a drug packing paper, and an image thereof was taken with a digital camera. Based on the image, the number of seeds supplied to the lipid analysis was measured, and this number was used in the correction of the lipid content per 100 grains of seeds described below.

(2) Gas Chromatographic (GC) Analysis

The methyl-esterified samples obtained above were analyzed by Gas chromatographic (GC). The GC was carried out using column: DB1-MS (J&W Scientific, Inc., Folsom, Calif.) and analysis apparatus: 6890 (Agilent Technologies, Inc., Santa Clara, Calif.), under the conditions as follows: [column oven temperature: maintained for 1 min at 100° C.→100° C. to 300° C. (temperature increase at 10° C./min) →maintained for 5 min at 300° C. (post-run for 2 min), injection port detector temperature: 300° C., injection method: split mode (split ratio=193:1), amount of sample injection 1 μL to 2 μL, column flow rate: constant at 0.5 mL/min, detector: FID, carrier gas: hydrogen, makeup gas: helium]. Amounts of fatty acid methyl esters were quantitatively determined based on the peak areas of the waveform data obtained by the GC analysis. The peak areas corresponding to the individual fatty acids were compared with that of 7-pentadecanone as the internal standard, and carried out corrections between the samples, and then the contents of the individual fatty acids in the whole seeds supplied to the analysis were calculated. Further, the contents of the individual fatty acids per 100 grains of seeds were calculated by dividing the calculated fatty acid contents by the number of seeds previously measured. Meanwhile, the peak of GC corresponding to the individual fatty acid in the seeds was identified by the retention time (RT) of a methyl ester of a standard product of the individual fatty acid, and by the analysis by GC/MS described below.

(3) GC/MS Analysis

The samples after the GC analysis were supplied to GC/mass spectrometrc (MS) analysis, if needed. The GC/MS analysis was carried out using capillary column: DB1-MS, GC analysis apparatus: 7890A (Agilent Technologies, Inc.), and MS analysis apparatus: 5975C (Agilent Technologies, Inc.) under the following conditions: [column oven temperature: maintained for 2 min at 100° C.→100° C. to 300° C. (temperature increase at 10° C./min)→maintained for 5 min at 300° C. (equilibration time 2 min, post-run for 5 min at 320° C.) or maintained for 2 min at 100° C.→100° C. to 200° C. (temperature increase 10° C./min)→200° C. to 320° C. (temperature increase 50° C./min)→maintained for 5 min at 320° C. (equilibration time 2 min, post-run for 5 min at 320° C.), injection port detector temperature: 250° C., injection method: splitless mode, amount of sample injection: 1 μL, column flow rate: constant at 1 mL/min, detector: FID, carrier gas: hydrogen, makeup gas: helium, solvent retention time: 7 min or 3.5 min, ionization method: EI method, ion source temperature: 250° C., interface temperature: 300° C., measurement mode: scan mode (m/z: 20 to 550 or 10 to 550)].

Figure 3:
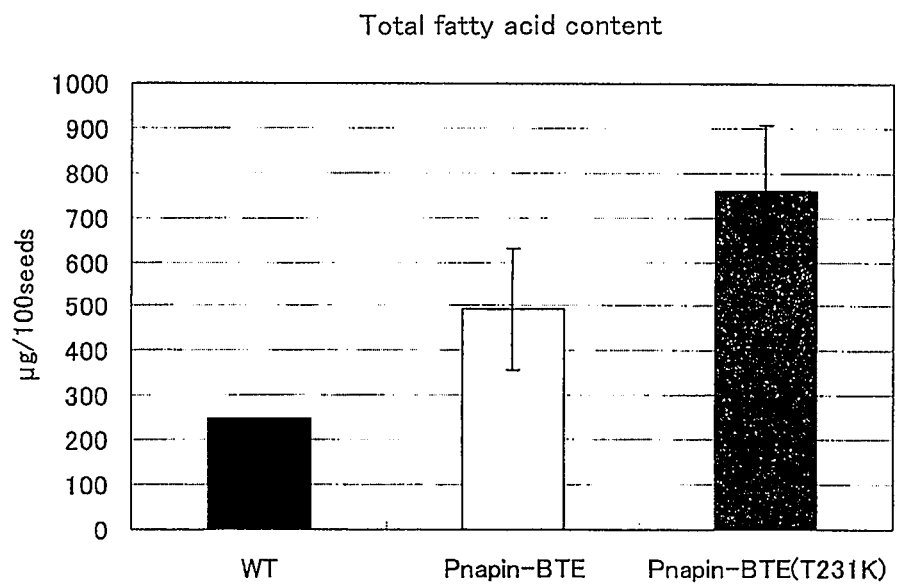
FIG. 3 is a diagram showing the total contents of the individual fatty acids contained in the seeds obtained from the wild strain of *Arabidopsis thaliana*: WT, *Arabidopsis thaliana* introduced with the wild-type thioesterase gene: Pnapin-BTE, and *Arabidopsis thaliana* introduced with the thioesterase variant gene: Pnapin-BTE (T231K).

The sum of fatty acid contents per 100 grains of seeds was calculated, by adding all the individual fatty acid contents in the seeds obtained by the GC analysis, and then normalizing the resultant with respect to the number of seeds supplied to the analysis. The sum of fatty acid contents calculated above was designated as the total fatty acid content (the total lipid content). As a negative control, the total lipid content per 100 grains of seeds of the wild strain of *Arabidopsis thaliana* was calculated in the same manner. The results are shown in FIG. 3. In FIG. 3, for the wild strain of *Arabidopsis thaliana*, the average value of the results obtained from two independent groups of seeds is shown, while for the BTE or BTE(T231K) transformant, the average value of five independent lines is shown. The error bars represent the standard deviations, and the value of p represents the results of Student's t-test between the transformants Pnapin-BTE and Pnapin-BTE (T231K).

As is apparent from FIG. 3, the seeds harvested from the transformant having the BTE gene or BTE(T231K) gene had a larger lipid content (total fatty acid content) as compared with the seeds of the wild strain of Arabidopsis thaliana. Further, the seeds harvested from the transformant Pnapin-BTE(T231K) having the BTE(T231K) gene accumulated a large amount of lipid therein as compared with the seeds of the transformant Pnapin-BTE having the BTE gene.

Reference Example 1

Construction of Transformant Having Thioesterase Variant (BTE(MRR197RRH)) Gene, and Production of Fatty Acids and Lipids in Transformant 1. Construction of Thioesterase Variant (BTE (MRR197RRH)) Gene Expression Plasmid A thioesterase variant BTE(MRR197RRH) was produced (SEQ ID NO: 27 and SEQ ID NO: 28). The thioesterase variant BTE(MRR197RRH) is a variant having two amino acid mutation in which methionine-arginine-arginine (MRR) at the $197^{th}$ to $199^{th}$ positions of the wild-type thioesterase gene, are substituted to arginine-arginine-histidine (RRH). The variant BTE(MRR197RRH) has threonine as the $231^{st}$ amino acid, and is not included in the thioesterase variants used in the present invention.

The wild-type thioesterase expression plasmid constructed in Example 1 was used as a template, and two divided gene fragments of the wild-type thioesterase were amplified by PCR using a pair of primers set forth in SEQ ID NO: 5 as shown in Table 1 of Example 1 and SEQ ID NO: 29 as shown in the following Table 3, and a pair of primers set forth in SEQ ID NO: 6 as shown in Table 1 of Example 1 and SEQ ID NO: 30 as shown in the following Table 3. The obtained two fragments were used as templates, and splicing overlap extension (SOE) PCR (Horton et al., Gene, 77, 61-68, 1989) was carried out by using a pair of oligonucleotide primers set forth in SEQ ID NO: 5 and SEQ ID NO: 6 as shown in Table 1. As a result, a gene fragment of the thioesterase variant BTE (MRR197RRH) was obtained, in which the nucleotide sequence ATG (Met) at the $589^{th}$ to $591^{st}$ positions were substituted by CGG (Arg), and the nucleotide sequence CGT (Arg) at the $595^{th}$ to $597^{th}$ positions were substituted by CAT (His) in the wild-type thioesterase set forth in SEQ ID NO: 28. The DNA fragment thus obtained was digested with restriction enzyme Xba I. Further, the plasmid vector pBluescriptII SK(−) (Stratagene Corp.) was also digested with Xba I, and then was subjected to dephosphorylation treatment. These two digestion products were linked by ligation, and the thioesterase variant gene fragment was inserted into Xba I site of the pBluescriptII SK(−). As a result, a plasmid which expresses the thioesterase variant BTE(MRR197RRH) in the form of being fused to the $27^{th}$ amino acid on the N-terminal side of the vector-derived LacZ protein, was constructed.

TABLE 3

| | Primer sequence (5'-3') |
|---|---|
| SEQ ID NO: 29 | CGGACAAGGAAATCATGTCGCCGGCCATTATTTCCAGATGCACCA |
| SEQ ID NO: 30 | CGGCGACATGATTTCCTTGTCCGGGACTGC |

2. Induction of Expression of Transformant Having Thioesterase Variant (BTE(MRR197RRH)) Gene An Escherichia coli mutant strain, strain K27 (fadD88) (Overath et al, Eur, J. Biochem. 7, 559-574, 1969), was transformed by using the plasmid that express the thioesterase variant BTE(MRR197RRH) constructed in the above section 1. The transformed strain K27 was left to stand overnight at 30° C., and those colonies thus obtained were inoculated in 1 mL of LBAmp liquid medium (Bacto Trypton 1%, yeast extract 0.5%, NaCl 1%, and ampicillin sodium 50 μg/mL), and was subjected to shaking culture for 12 hours at 30° C. After 12 hours, 25 μL of the culture fluid was added to another 2.5 mL of LBAmp liquid medium, and the mixture was subjected to shaking culture at 30° C. After a lapse of 15 hours from the initiation of culture, the contents of the individual fatty acids and the total fatty acid content in the culture fluid were analyzed in the same method described above sections 4. and 5. of Example 1. Further, after a lapse of 15 hours from the initiation of culture, the light absorbance at 600 nm (OD600) of the culture fluid was measured to calculate the cell numbers of Escherichia coil contained in the culture fluid. As a negative control, Escherichia coli strain K27 that was transformed with plasmid vector pBluescriptII SK(−), and the transformants each of which has the wild-type thioesterase (BT) gene or the thioesterase variant (BTE (T231K)) gene used in the present invention, were also subjected to the same experiment.

The total fatty acid content of each sample was calculated by summing the contents of the individual fatty acids ranging from C12:0 to C18:1 in the culture fluid. The results are shown in FIG. 4.

Figure 4:
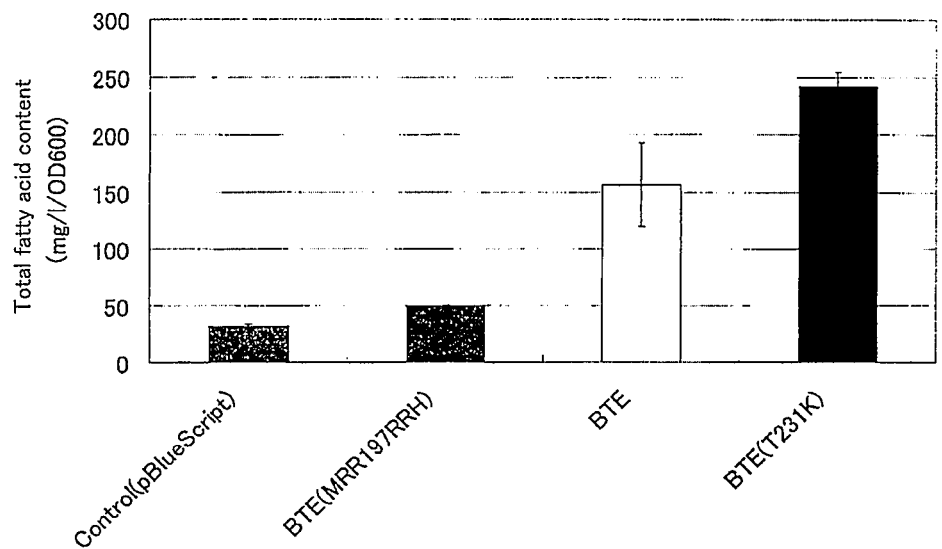
FIG. 4 is a diagram comparing the total contents of the individual fatty acids in *Escherichia coli* introduced with thioesterase variant (BTE(MRR197RRH)) gene, *Escherichia coli* introduced with the wild-type thioesterase (BTE) gene, and *Escherichia coli* introduced with thioesterase variant (BTE(T231K)) gene. Meanwhile, the total content of the individual fatty acids was calculated by summing the contents of the individual fatty acids ranging from C12:0 to C18:1. The error bars in the diagram represent the standard deviations calculated from the total contents of the individual fatty acids included in the culture fluids derived from three independently clones.

As is apparent from FIG. 4, the total content (total amount of production) of lipids in the transformant having the BTE (MRR197RRH) gene was almost the same as that of the control, and greatly decreased by about one-third as compared with that of the transformant having the BTE gene, and by about one-fifth as compared with that of the transformant having the BTE(T231K) gene.

INDUSTRIAL APPLICABILITY

The method of the present invention for producing fatty acids or lipids containing fatty acids has excellent productivity, and the fatty acids or lipids obtained by the method can be utilized for food, an emulsifier for cosmetic products and the like, a cleansing agent such as a soap or a detergent, a fiber treatment agent, a hair conditioning agent, a disinfectant, an antiseptic, and the like.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2009-295458 filed in Japan on Dec. 25, 2009, and Patent Application No. 2010-227262 filed in Japan on Oct. 7, 2010, each of which is entirely herein incorporated by reference.

What is claimed is:

1. A method of producing a fatty acid or a lipid containing a fatty acid, comprising;
   i, introducing a gene that encodes any one of the thioesterase variants of the following (a) to (d) into a plant as a hast;
   ii. obtaining a transformed plant in which the total fatty acid content in the plant's seeds is enhanced as compared to that in seeds from the same plant transformed with wild-type thioesterase having the amino acid sequence of SEQ ID NO:1; and
   iii. collecting a fatty acid, or a lipid containing a fatty acid, from the seeds of the transformed plant thus obtained,
   wherein said thioesterase variants are selected from the group consisting of
   (a) a thioesterase variant comprising the amino acid sequence set forth in SEQ ID NO: 1, except that the $231^{st}$ amino acid of the amino acid sequence of SEQ ID NO: 1 is substituted from threonine to lysine;
   (b) a thioesterase variant as in part (a) but also comprising one to ten amino acids other than the $231^{st}$ amino acid of the amino acid sequence of SEQ ID NO: I that are deleted, substituted, inserted and/or added in the amino acid sequence of the variant of part (a);
   (c) a thioesterase variant comprising the amino acid sequence set forth in the $84^{th}$ to $382^{nd}$ amino acids of the amino acid sequence set forth in SEQ ID NO: 1 except that the amino acid at position 231 in the amino acid sequence of SEQ ID NO: 1 is substituted from threonine to lysine; and
   (d) a thioesterase variant as in part (c) but also comprising one to ten amino acids other than the $231^{st}$ amino acid that are deleted, substituted, inserted and/or added in the amino acid sequence of the variant of part (c).

2. The method of producing a fatty acid or a lipid containing a fatty acid according to claim 1, wherein the fatty acid comprises a long-chain fatty acid having 12 or more carbon atoms.

3. The method of producing a fatty acid or a lipid containing a fatty acid according to claim 2, wherein the fatty acid is lauric acid.

4. The method of producing a fatty acid or a lipid containing a fatty acid according to claim 1, wherein the plant is *Arabidopsis thaliana*.

5. A method of enhancing productivity of a lipid containing a fatty acid in a plant's seeds, comprising:
   introducing a gene that encodes any one of the thioesterase variants of the following (a) to (d) into a plant as a host; and
   obtaining a transformed plant in which the total fatty acid content in the plant's seeds is enhanced as compared to that in seeds from the same plant transformed with wild-type thioesterase having the amino acid sequence of SEQ ID NO:1;
   wherein said thioesterase variants are selected from the group consisting of
   (a) a thioesterase variant comprising the amino acid sequence set forth in SEQ ID NO:1, except that the 231" amino acid of the amino acid sequence of SEQ ID NO: 1 is substituted from threonine to lysine;
   (b) a thioesterase variant as in part (a) but also comprising one to ten amino acids other than the 231" amino acid of the amino acid sequence of SEQ ID NO: I that are deleted, substituted, inserted and/or added in the amino acid sequence of the variant of part (a);
   (c) a thioesterase variant comprising the amino acid sequence set forth in the $84^{th}$ to $382^{nd}$ amino acids of the amino acid sequence set forth in SEQ ID NO: 1 except that the amino acid at position 231 in the amino acid sequence of SEQ ID NO: 1 is substituted from threonine to lysine; and
   (d) a thioesterase variant as in part (c) but also comprising one to ten amino acids other than the $231^{st}$ amino acid that are deleted, substituted, inserted and/or added in the amino acid sequence of the variant of part (c).

6. A transformed plant cell into which a gene has been introduced that encodes a thioesterase variant selected from the group consisting of:
   (a) a thioesterase variant comprising the amino acid sequence set forth in SEQ ID NO: 1, except that the $231^{st}$ amino acid of the amino acid sequence of SEQ ID NO: 1 is substituted from threonine to lysine;
   (b) a thioesterase variant as in part (a) but also comprising one to ten amino acids other than the 231" amino acid of the amino acid sequence of SEQ ID NO: 1 that are deleted, substituted, inserted and/or added in the amino acid sequence of the variant of part (a);
   (c) a thioesterase variant comprising the amino acid sequence set forth in the $84^{th}$ to $382^{nd}$ amino acids of the amino acid sequence set forth in SEQ ID NO: 1 except that the amino acid at position 231 in the amino acid sequence of SEQ ID NO: 1 is substituted from threonine to lysine; and
   (d) a thioesterase variant as in part (c) but also comprising one to ten amino acids other than the $231^{st}$ amino acid that are deleted, substituted, inserted and/or added in the amino acid sequence of the variant of part (c);
   wherein the total fatty acid content in the plant's seeds is enhanced as compared to that in seeds from the same plant transformed with wild-type thioesterase having the amino acid sequence of SEQ ID NO:1.

7. The transformed plant according to claim 6, wherein the plant is *Arabidopsis thaliana*.

8. The method of producing a fatty acid or a lipid containing a fatty acid according to claim 1,
   wherein the thioesterase variant is a thioesterase variant comprising an amino acid sequence in which the $231^{st}$ amino acid is substituted from threonine to lysine in the amino acid sequence set forth in SEQ ID NO:1, and further in which the amino acids at specific positions in the amino acid sequence set forth in SEQ ID NO: 1 are as follows:
   the $113^{rd}$ amino acid is valine or isoleucine;
   the $114^{th}$ amino acid is arginine;
   the $117^{th}$ amino acid is glutamic acid;
   the $118^{th}$ amino acid is valine or isoleucine;
   the $134^{th}$ amino acid is glutamine or arginine;
   the $135^{th}$ amino acid is glutamic acid or aspartic acid;
   the $136^{th}$ amino acid is threonine or alanine;
   the $145^{th}$ amino acid is glycine;
   the $154^{th}$ amino acid is threonine or alanine;
   the $162^{nd}$ amino acid is leucine;
   the $163^{rd}$ amino acid is isoleucine, phenylalanine or methionine;
   the $165^{th}$ amino acid is valine;
   the $176^{th}$ amino acid is tyrosine or histidine;
   the $177^{th}$ amino acid is proline;
   the $179^{th}$ amino acid is tryptophan;
   the $181^{st}$ amino acid is glutamic acid, aspartic acid or asparagine;
   the $185^{th}$ amino acid is isoleucine, valine or methionine;
   the $201^{st}$ amino acid is tryptophan or phenylalanine;
   the $215^{th}$ amino acid is alanine or cysteine;
   the $216^{th}$ amino acid is serine or threonine;

the 217th amino acid is serine;
the 222$^{nd}$ amino acid is methionine;
the 226$^{th}$ amino acid is threonine;
the 227$^{th}$ amino acid is arginine or lysine;
the 229$^{th}$ amino acid is leucine, phenylalanine or isoleucine;
the 239$^{th}$ amino acid is glutamic acid or lysine;
the 257$^{th}$ amino acid is lysine or arginine;
the 260$^{th}$ amino acid is lysine, arginine or histidine;
the 300$^{th}$ amino acid is proline;
the 309$^{th}$ amino acid is leucine or isoleucine;
the 314$^{th}$ amino acid is leucine, methionine or valine;
the 315$^{th}$ amino acid is glutamic acid or aspartic acid,
the 316$^{th}$ amino acid is tyrosine;
the 317$^{th}$ amino acid is arginine or lysine,
the 318$^{th}$ amino acid is arginine or lysine; and
the 319$^{th}$ amino acid is glutamic acid.

9. The method of producing a fatty acid or a lipid containing a fatty acid according to claim 8, wherein the fatty acid comprises a long-chain fatty acid having 12 or more carbon atoms.

10. The method of producing a fatty acid or a lipid containing a fatty acid according to claim 9, wherein the fatty acid is lauric acid.

11. The method of producing a fatty acid or a lipid containing a fatty acid according to claim 8, wherein the plant is *Arabidopsis thaliana*.

12. The method of producing a fatty acid or a lipid containing a fatty acid according to claim 1, wherein the amino acid sequence of the variant comprises the amino add sequence of the 84$^{th}$ to 230$^{th}$ amino acids and 232$^{nd}$ to 382$^{nd}$ amino acids of said SEQ ID NO:1.

13. The method of producing a fatty acid or a lipid containing a fatty acid according to claim 12, wherein the fatty acid comprises a long-chain fatty acid having 12 or more carbon atoms.

14. The method of producing a fatty acid or a lipid containing a fatty acid according to claim 13, wherein the fatty acid is lauric acid.

15. The method of producing a fatty acid or a lipid containing a fatty acid according to claim 12, wherein the plant is *Arabidopsis thaliana*.

16. The method of producing a fatty acid or a lipid containing a fatty acid according to claim 1, wherein the nucleotide sequence of the gene that encodes the thioesterase variant is selected from the following (d) to (g):
(d) A nucleotide sequence comprising the nucleotide sequence of SEQ ID NO:2 but in which the 691$^{st}$ to 693$^{rd}$ nucleotides encoding threonine are substituted by nucleotides encoding lysine in the nucleotide sequence set forth in SEQ ID NO:2;
(e) A nucleotide sequence as in (d) but also comprising one to ten nucleotides, other than the 691$^{st}$ to 693$^{rd}$ nucleotides, that are deleted, substituted, inserted, and/or added in the nucleotide sequence of the above item (d);
(f) A nucleotide sequence comprising the nucleotide sequence set forth in the 250$^{th}$ to 149$^{th}$ nucleotides of the nucleotide sequence set forth in SEQ ID NO: 2 except that the 691$^{st}$ to 693$^{rd}$ nucleotides that encode threonine in SEQ ID NO:2 have been substituted by nucleotides that encode lysine; and
(g) A nucleotide sequence as in part (f) but also comprising one to ten nucleotides, other than the 691$^{st}$ to 693$^{rd}$ nucleotides, that are deleted, substituted, inserted and/or added in the nucleotide sequence of part (f).

17. The method of producing a fatty acid or a lipid containing a fatty acid according to claim 16, wherein the fatty acid comprises a long-chain fatty acid having 12 or more carbon atoms.

18. The method of producing a fatty acid or a lipid containing a fatty acid according to claim 17, wherein the fatty acid is lauric acid.

19. The method of producing a fatty acid or a lipid containing a fatty acid according to claim 16, wherein the plant is *Arabidopsis thaliana*.

20. The method of producing a fatty acid or a lipid containing a fatty acid according to claim 1, wherein the gene that encodes the thioesterase variant comprises a promoter selected from the group consisting of the lac promoter, a trp promoter, a tac promoter, a trc promoter, a T7 promoter, a SpoVG promoter, a cauliflower mosaic virus 35S RNA promoter, a promoter for a housekeeping gene, the rapeseed-derived Napin gene promoter, and a plant-derived Rubisco promoter.

* * * * *